Figure 1:
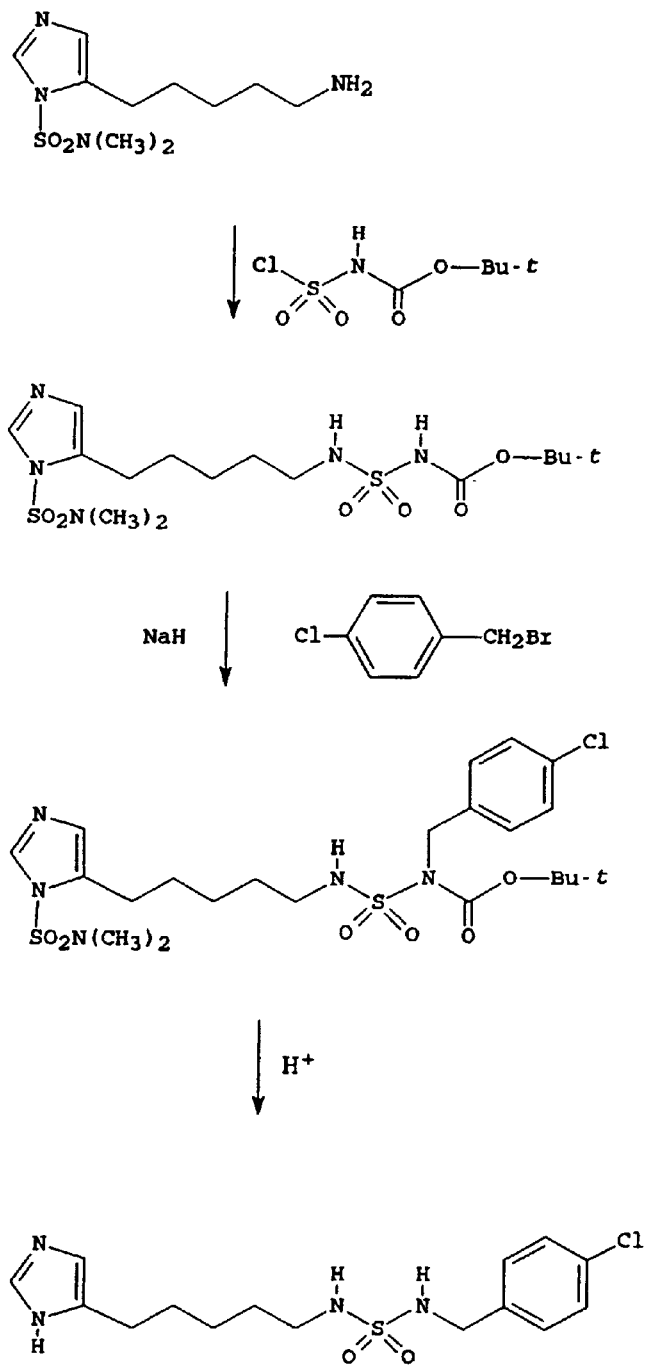

United States Patent

Kalindjian et al.

[11] Patent Number: 6,080,871
[45] Date of Patent: Jun. 27, 2000

[54] SULFONAMIDES AND SULFAMIDES AS $H_3$ RECEPTOR ANTAGONISTS

[75] Inventors: Sarkis Barret Kalindjian, Surrey; Nigel Paul Shankley, Tonbridge; Matthew John Tozer, London; Iain Mair McDonald; Michael John Pether, both of Kent; Elaine Anne Harper, Beds; Gillian Fairfull Watt, Surrey; Tracey Cooke, Herts; Caroline Minli Rachel Low, London, all of United Kingdom

[73] Assignee: James Black Foundation Limited, Dulwich, United Kingdom

[21] Appl. No.: 09/117,808

[22] PCT Filed: Feb. 10, 1997

[86] PCT No.: PCT/GB97/00358

§ 371 Date: Oct. 6, 1998

§ 102(e) Date: Oct. 6, 1998

[87] PCT Pub. No.: WO97/29092

PCT Pub. Date: Aug. 14, 1997

[30] Foreign Application Priority Data

Feb. 9, 1996 [GB] United Kingdom ............ 9602649
Nov. 21, 1996 [GB] United Kingdom ............ 9624215

[51] Int. Cl.[7] ............ C07D 233/64; C07D 401/12; A61K 31/4164
[52] U.S. Cl. ............ 548/335.5; 514/399; 514/400; 514/311; 514/397; 546/14; 546/153; 548/110; 548/311.1; 548/312.1
[58] Field of Search ............ 548/335.5, 312.1, 548/311.1, 110; 514/399, 400, 311, 397; 546/14, 153

[56] References Cited

U.S. PATENT DOCUMENTS

| | | | |
|---|---|---|---|
| 2,372,066 | 3/1945 | Fell ................................. | 548/335.5 X |
| 3,497,591 | 2/1970 | Yankell et al. ................ | 548/325.5 X |
| 5,447,728 | 9/1995 | Milstein et al. .................. | 424/498 |

FOREIGN PATENT DOCUMENTS

| | | |
|---|---|---|
| 0082648 | 6/1983 | European Pat. Off. . |
| 0193904 | 9/1986 | European Pat. Off. . |
| 3219113 | 11/1983 | Germany . |
| 93/14070 | 7/1993 | WIPO . |
| 95/06037 | 3/1995 | WIPO . |

OTHER PUBLICATIONS

Aleksiev et al, Chemical Abstracts, vol. 79 (6) #092556t, (1973).
Chemical Substances, Chem. Abstracts, 9th Coll. Index, vol. 76–85, 18750CS, 1972–1976.
Database Crossfire, Beilstein Informations System XP002030845, (1971).
Database Crossfire, Beilstein Information System XP002030846, (1981).
Griffith, J. Amer. Chem. Soc., vol. 79, pp. 639–644, (1957).
Imab, et al, J. Antibiot., vol. 44, pp. 76–85. (1991).
Lee et al, Chemical Abstracts, vol. 117, #163157e, (1992).
Chem. Abstr., Chemical Subst. Index, vol. 116, pp. 5046c, pp. 5047CS, 5051CS, (1992).
Liao et al, Chemical Abstracts, vol. 103, #101248n, (1985).
Chem. Abstr., Chemical Substances, 11th Coll. Ind., vol. 96–105, p. 32773CS, (1982–1986).
Nishizawa et al, Chemical Abstracts, vol. 116, #247605s, (1992).
Chem Abstr., Chemical Substances, Index, vol. 116, pp. 5046C, 5047CS, 5051CS, (1992).
Reshetova et al, Chemical Abstracts, vol. 106, #210288h, (1987).

(List continued on next page.)

*Primary Examiner*—Floyd D. Higel
*Attorney, Agent, or Firm*—Foley & Lardner

[57] ABSTRACT

Compounds of formula (I) or (II) wherein $R^1$ is $C_4$ to $C_{20}$ hydrocarbyl (in which one or more hydrogen atoms may be replaced by halogen, and up to three carbon atoms may be replaced by oxygen, nitrogen or sulphur atoms, provided that $R^1$ does not contain an —O—O— group), $R^2$ is H or $C_1$ to $C_3$ alkyl, m is from 1 to 15, n is from 2 to 6, each X group is independently (a), or one X group is —N($R^4$)—, —O— or —S— and the remaining X groups are independently (a), wherein $R^3$ is H, $C_1$ to $C_6$ alkyl, —$CO_2R^5$, —$CONR^5_2$, —$CR^5_2OR^6$ or —$OR^5$ (in which $R^5$ and $R^6$ are H or $C_1$ to $C_3$ alkyl), and $R^4$ is H or $C_1$ to $C_6$ alkyl, each Y group is independently —C($R^3$)$R^4$—, or up to two Y groups are —N($R^4$)—, —O— or —S— and the remaining Y groups are independently —C($R^3$)$R^4$—, wherein $R^3$ is as defined above, one $R^4$ group in the structure is imidazoyl or imidazoylalkyl and the remaining $R^4$ groups are H or $C_1$ to $C_6$ alkyl, and Z is >C($R^7$)$NR^2$— or >N—, wherein $R^7$ is any of the groups recited above for $R^3$, and pharmaceutically acceptable salts thereof are ligands at histamine $H_3$ receptors.

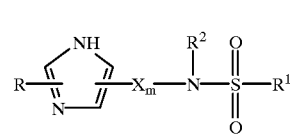

(I)

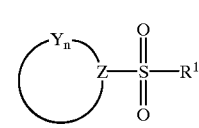

(II)

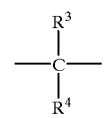

(a)

23 Claims, 2 Drawing Sheets

OTHER PUBLICATIONS

Chem Abstr. Chemical Substances, $13^{th}$ Coll. vol. Ind, vol. 106–115, p. 44639CS, (1987–1991).

Serebryanyi et al, Chemical Abstracts, vol. 56, 4853f, (1962).

Tochilkin et al, Chemical Abstracts, vol. 113, # 164723r, (1990).

Shigematsu et al, Tetrahedron Letters, vol. 29 (40), pp. 5147–5150, (1988).

Ung et al, Tetrahedron Letters, vol. 37 (34), pp. 6209–6212, (1996).

Warshawsky et al, Synthesis, vol. of 1989, No. 11, pp. 825–829, (1989).

SULFONAMIDES AND SULFAMIDES AS H₃ RECEPTOR ANTAGONISTS

This application is a '371 of PCT/GB97/00358 filed Feb. 10, 1997.

This invention relates to compounds which bind to histamine H₃ receptors, and to methods of making such compounds.

Histamine is well known as a mediator in certain hypersensitive reactions of the body, such as allergic rashes, hayfever and asthma. These conditions are now commonly treated with potent antagonists of histamine, so-called "antihistamines".

In the 1940s, it was noted that some physiological effects of histamine, such as increased gastric acid secretion and cardiac stimulation, were not blocked by the antihistamines which were then available. This led to the proposal that histamine receptors exist in at least two distinct types, referred to as H, and H2 receptors. Subsequently, H₂ antagonists (such as cimetidine, ranitidine and famotidine) were identified, and they have become important in the treatment of gastric ulcers.

In the early 1980s, it was established that histamine also has a role as a neurotransmitter in the central nervous system. Arrang et al., *Nature* 302, 832 to 837 (1983), proposed the existence of a third histamine receptor subtype (H3) located presynaptically on histaminergic nerve endings. Arrang et al. postulated that the H₃ receptor is involved in inhibiting the synthesis and release of histamine in a negative feedback mechanism. The existence of the H₃ receptor was subsequently confirmed by the development of selective H₃ agonists and antagonists (Arrang et al., *Nature* 327, 117 to 123 (1987)). The H₃ receptor has subsequently been shown to regulate the release of other neurotransmitters both in the central nervous system and in peripheral organs, in particular in the lungs and GI tract. In addition, H₃ receptors are reported to regulate the release of histamine from mast cells and enterochromaffin-like cells.

A need exists for potent and selective H₃ ligands (both agonists and antagonists) as tools in the study of the role of histamine as a neurotransmitter, and in its roles as a neuro, endo- and paracrine hormone. It has also been anticipated that H₃ ligands will have therapeutic utility for a number of indications including use as sedatives, sleep regulators, anticonvulsants, regulators of hypothalamo-hypophyseal secretion, antidepressants and modulators of cerebral circulation, and in the treatment of asthma and irritable bowel syndrome.

A number of imidazole derivatives have been proposed in the patent literature as H₃ ligands. Representative are the disclosures of EP-A-0197840, EP-A-0214058, EP-A-0458661, EP-A-0494010, EP-A-0531219, WO91/17146, WO92/15567, WO93/01812, WO93/12093, WO93/12107, WO93/12108, WO93/14070, WO93/20061, WO94/17058, WO95/06037, WO95/11894, WO95/14007, U.S. Pat. No. 4,988,689 and U.S. Pat. No. 5,217,986.

The present invention provides a new class of H₃ receptor ligands, having a sulfonamide or sulfamide group spaced from an imidazole ring.

According to the present invention, there is provided a compound of the formula

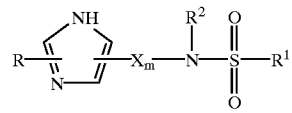

or

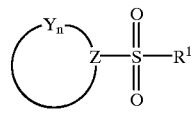

wherein

R represents from zero to two substituents selected from $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulphamoyl and cyano, $R^1$ is $C_1$ to $C_{20}$ hydrocarbyl (in which one or more hydrogen atoms may be replaced by halogen, and up to four carbon atoms [and especially from 0 to 3 carbon atoms] may be replaced by oxygen, nitrogen or sulphur atoms, provided that $R^1$ does not contain an —O—O— group), $R^2$ is H or $C_1$ to $C_{15}$ hydrocarbyl (in which one or more hydrogen atoms may be replaced by halogen, and up to three carbon atoms may be replaced by oxygen, nitrogen or sulphur atoms, provided that $R^2$ does not contain an —O—O— group), m is from 3 to 15 (preferably 3 to 10, eg. 4 to 9)

n is from 2 to 6, each X group is independently

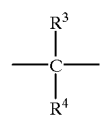

or one X group is —N($R^4$)—, —O— or —S— (provided that this X group is not adjacent the —NR²— group) and the remaining X groups are independently

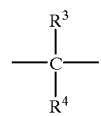

wherein $R^3$ is H, $C_1$ to $C_6$ alkyl, $C_2$ to $C_6$ alkenyl, —CO₂$R^5$, —CONR⁵₂, —CR⁵₂OR⁶ or —OR⁵ (in which $R^5$ and $R^6$ are H or $C_1$ to $C_3$ alkyl), and $R^4$ is H or $C_1$ to $C_6$ alkyl, each Y group is independently —C($R^3$)$R^4$—, or up to two Y groups are —N($R^4$)—, —O— or —S— and the remaining Y groups are independently —C($R^3$)$R^4$—, wherein $R^3$ is as defined above, one $R^4$ group in the structure is imidazoyl, imidazoylalkyl, substituted imidazoyl or substituted imidazoyl, and the remaining $R^4$ groups are H or $C_1$ to $C_6$ alkyl, and Z is >C(R$^7$)NR$^2$— or >N—, wherein R$^7$ is any of the groups recited above for R$^3$, and pharmaceutically acceptable salts thereof.

The invention also comprehends derivative compounds ("pro-drugs") which are degraded in vivo to yield the species of formula (I) or (II). Pro-drugs are usually (but not always) of lower potency at the target receptor than the species to which they are degraded. Pro-drugs are particularly useful when the desired species has chemical or physical properties which make its administration difficult or inefficient. For example, the desired species may be only poorly soluble, it may be poorly transported across the mucosal epithelium, or it may have an undesirably short plasma half-life. Further discussion of pro-drugs may be found in Stella, V. J. et al., "Prodrugs", *Drug Delivery Systems*, pp. 112–176 (1985), and Drugs, 29, pp. 455–473 (1985).

Pro-drug forms of the pharmacologically-active compounds of the invention will generally be compounds according to formula (I) or (II) having an acid group which is esterified or amidated. Included in such esterified acid groups are groups of the form —COOR$^8$, wherein R$^8$ is C$_1$ to C$_5$ alkyl, phenyl, substituted phenyl, benzyl, substituted benzyl, or one of the following:

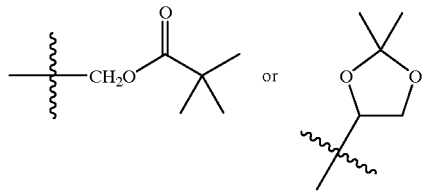

Amidated acid groups include groups of the formula —CONR$^9$R$^{10}$, wherein R$^9$ is H, C$_1$ to C$_5$ alkyl, phenyl, substituted phenyl, benzyl, or substituted benzyl, and R$^{10}$ is —OH or one of the groups just recited for R$^9$.

Compounds of formula (I) or (II) having an amino group may be derivatised with a ketone or an aldehyde such as formaldehyde to form a Mannich base. This will hydrolyse with first order kinetics in aqueous solution.

Pharmaceutically acceptable salts of the acidic compounds of the invention include salts with alkali meals and alkaline earth metals, such as sodium, potassium, calcium and magnesium, and salts with organic bases. Suitable organic bases include amines such as N-methyl-D-glucamine.

Pharmaceutically acceptable salts of the basic compounds of the invention include salts derived from organic or inorganic acids. Suitable acids include hydrochloric acid, hydrobromic acid, trifluoracetic acid, phosphoric acid, oxalic acid, maleic acid, succinic acid and citric acid.

The compounds of the invention may exist in various enantiomeric, diastereomeric and tautomeric forms. It will be understood that the invention comprehends the different enantiomers, diastereomers and tautomers in isolation from each other, as well as mixtures of enantiomers, diastereomers and tautomers.

The term "hydrocarbyl", as used herein, refers to monovalent groups consisting of carbon and hydrogen. Hydrocarbyl groups thus include alkyl, alkenyl, and alkynyl groups (in both straight and branched chain forms), cycloalkyl (including polycycloalkyl), cycloalkenyl, and aryl groups, and combinations of the foregoing, such as alkylaryl, alkenylaryl, alkynylaryl, cycloalkylaryl, and cycloalkenylaryl groups, A "carbocyclic" group, as the term is used herein, comprises one or more closed chains or rings, which consist entirely of carbon atoms. Included in such groups are alicyclic groups (such as cyclopropyl, cyclobutyl, cyclopentyl, cyclohexyl and adamantyl), groups containing both alkyl and cycloalkyl moieties (such as adamantanemethyl), and aromatic groups (such as phenyl, naphthyl, indanyl, fluorenyl, (1,2,3,4)-tetrahydronaphthyl, indenyl and isoindenyl).

The term "aryl" is used herein to refer to aromatic carbocyclic groups, including those mentioned above.

A "heterocyclic" group comprises one or more closed chains or rings which have at least one atom other than carbon in the closed chain or ring. Examples include benzimidazolyl, thienyl, furanyl, pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, piperazinyl, morpholinyl, thionaphthyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, naphthridinyl, cinnolinyl, quinazolinyl, pyridopyridyl, benzoxazinyl, quinoxadinyl, chromenyl, chromanyl, isochromanyl and carbolinyl.

When reference is made herein to a substituted carbocyclic group (such as substituted phenyl) or a substituted heterocyclic group, the substituents are preferably from 1 to 3 in number and selected from C$_1$ to C$_6$ alkyl, C$_1$ to C$_6$ alkoxy, C$_1$ to C$_6$ alkylthio, carboxy, C$_1$ to C$_6$ carboalkoxy, nitro, trihalomethyl, hydroxy, amino, C$_1$ to C$_6$ alkylamino, di(C$_1$ to C$_6$ alkyl)amino, aryl, C$_1$ to C$_6$ alkylaryl, halo, sulphamoyl and cyano. The moiety R, when present, represents one or two of the foregoing groups, and preferably C$_1$ to C$_3$ alkyl or halo.

The term "halogen", as used herein, refers to any of fluorine, chlorine, bromine and iodine.

Preferably, R$^2$ is selected from H, C$_1$ to C$_6$ alkyl, C$_1$ to C$_6$ cycloalkyl, C$_1$ to C$_6$ hydroxyalkyl, C$_1$ to C$_6$ alkylhydroxyalkyl, aryl C$_1$ to C$_6$ alkyl and substituted aryl C$_1$ to C$_6$ alkyl. For example, R$^2$ may be H or C$_1$ to C$_3$ alkyl.

In certain embodiments, —X$_m$— is a C$_1$ to C$_8$ alkylene group, eg a butylene group.

Included in the definition of R$^1$ are aryl-containing groups (such as phenyl, substituted phenyl, naphthyl and substituted naphthyl), and (cycloalkyl)alkyl groups (such as cyclohexylpropyl and adamantylpropyl).

Preferably, R$^1$ is a group of the formula

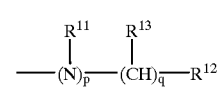

III wherein
p is 0 or 1,
R$^{11}$ is H or C$_1$ to C$_3$ alkyl,
q is from 0 to 4,
R$^{12}$ is a carbocyclic, substituted carbocyclic, heterocyclic or substituted heterocyclic group, and
R$^{13}$ is independently selected from H, C$_1$ to C$_6$ alkyl, C$_1$ to C$_6$ cycloalkyl, C$_1$ to C$_6$ hydroxyalkyl, C$_1$ to C$_6$ alkylhydroxyalkyl, aryl C$_1$ to C$_6$ alkyl and substituted aryl C$_1$ to C$_6$ alkyl.

Preferably, R$^{13}$ is hydrogen.

Imidazoylalkyl groups in the compounds of the invention usually have from 1 to 8 carbon atoms in the alkyl chain.

We have found that a number of compounds in the prior art have shown a significant discrepancy in their activity as measured by two ileum based assays which are described below. Analysis of data obtained in these particular functional and radioligand binding assays and also in other related bioassays suggests that the discrepancy may be connected, at least in part, with residual efficacy inherent in these structures. In practice, this means that these particular compounds may act as agonists, at least in some tissues.

Surprisingly, we have found that when m is 3 or more, preferably from 3 to 9, and especially from 4 to 8, the compounds disclosed herein do not show a significant discrepancy in the two assays. Thus, these compounds may be considered to be true antagonists with respect to the action of the native hormone, rather than having the potential to act as partial or full agonists. In one aspect, therefore, the present invention provides the use of these compounds as histamine antagonists, and in the manufacture of medicaments for this purpose.

The compounds of the invention which are sulfonamides may be prepared by reacting a suitably protected derivative of a compound of the formula

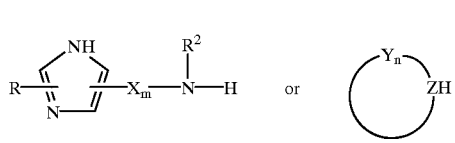

IV with a sulfonyl chloride of the formula $R^1SO_2Cl$. Suitable protecting groups for the imidazole moiety include trityl and N,N-dimethylsulfamoyl groups. Any other functional groups in the reactants may be protected by reagents well known to those in the art.

The reaction with the sulfonyl chloride is carried out in a suitable non-aqueous solvent such as dried N,N-dimethylformamide or dried dichloromethane, in the presence of a base such as triethylamine. Typically, the reaction is carried out at room temperature for a period of several hours.

Compounds of the invention which are sulfamides may conveniently be prepared by
 a) reacting chlorosulfonyl isocyanate with an appropriate alcohol of the formula $R^{14}OH$,
 b) reacting the product of step a) with a suitably protected derivative of a compound of formula IV above,
 c) reacting the product of step b) with a base such as sodium hydride and then a compound of formula $R^1$—Br, wherein the bromine atom is attached to a carbon atom of $R^1$, and
 d) treating the product of step c) with acid to remove the $R^{14}OCO$— group, and other protecting groups.

In preferred embodiments, the reagent in step c) is of the formula

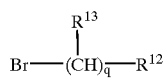

wherein q, $R^{12}$ and $R^{13}$ are as defined above.

Particularly preferred alcohols for use in step a) are t-butanol and benzyl alcohol.

FIG. 1 illustrates the synthesis of N-[5-(4(5)-imidazoyl) pentyl]-N'-(4-chlorophenyl)methyl-sulfamide by this method.

In an alternative process, sulfamides according to invention may be prepared by
 a) reacting chlorosulfonyl isocyanate with an appropriate alcohol of the formula $R^{14}OH$,
 b) reacting the product of step a) with a suitably protected derivative of a compound of the formula $R^1$—H, wherein the hydrogen atom is attached to a nitrogen atom of $R^1$,
 c) reacting the product of step b) with a suitably protected derivative of a compound of formula

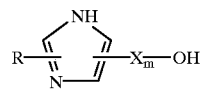

and
 d) treating the product of step c) with acid to remove the $R^{14}OCO$— group, and other protecting groups.

In preferred embodiments, the reagent used in step b) is of the formula

Figure 2:
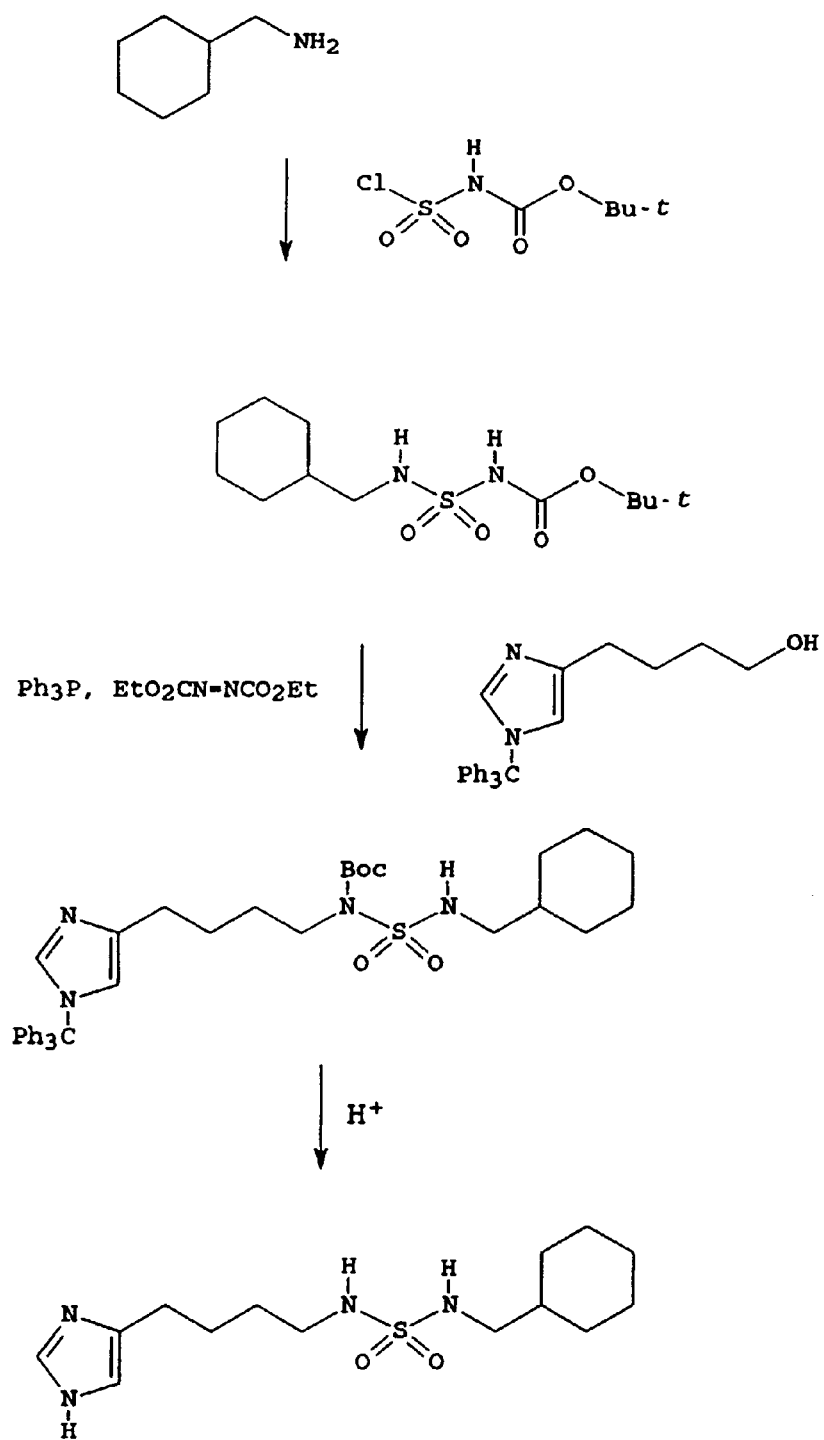

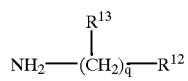

wherein q, $R^{12}$ and $R^{13}$ are as defined above. FIG. 2 illustrates the synthesis of N-[4-(4(5)-imidazoyl)butyl]-N'-cyclohexylmethylsulfamide by this method.

Pharmaceutically acceptable salts of the acidic or basic compounds of the invention can of course be made by conventional procedures, such as by reacting the free base or acid with at least a stoichiometric amount of the desired salt-forming acid or base.

It is anticipated that the compounds of the invention can be administered by oral or parenteral routes, including intravenous, intramuscular, intraperitoneal, subcutaneous, rectal and topical administration.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

Effective doses of the compounds of the present invention may be ascertained by conventional methods. The specific dosage level required for any particular patient will depend on a number of factors, including the severity of the condition being treated, the route of administration and the weight of the patient. In general, however, it is anticipated that the daily dose (whether administered as a single dose or as divided doses) will be in the range 0.001 to 5000 mg per day, more usually from 1 to 1000 mg per day, and most usually from 10 to 200 mg per day. Expressed as dosage per unit body weight, a typical dose will be expected to be between 0.01 µg/kg and 50 mg/kg, especially between 10 µg/kg and 10 mg/kg, eg. between 100 µg/kg and 2 mg/kg.

The invention is now further illustrated by means of the following examples.

EXAMPLE 1

N-[2-(4(5)-Imidazoyl)ethyl]-2-naphthalenesulfonamide

To a suspension of histamine (824 mg, 7.41 mmol) in dried N,N-dimethylformamide (10 ml) was added triethylamine (2.07 ml, 14.8 mmol) and 2-naphthalenesulfonyl chloride (1.68 g, 7.41 mmol). The mixture was stirred at room temperature for 48 h, poured into water (50 ml) and extracted with ethyl acetate (3×20 ml). The combined organic extracts were washed with brine (3×20 ml), the solvent evaporated under reduced pressure and the residue purified by flash column chromatography (silica, 1% $NH_3$ aq (880)/10% MeOH/$CH_2Cl_2$). The resultant oil ($R_f$ 0.17) was crystallized from tetrahydrofuran to afford the title compound as a white solid, (440 mg, 20%): $^1$H NMR (300 Hz, $d_6$-DMSO) 11.73(1H, s), 8.41 (1H, s), 8.13(2H, m), 8.02 (1H, d), 7.80(1H, dd), 7.67(2H, m), 7.44(1H, d), 6.74(1H, s), 2.99(2H, t), 2.58(2H, t). The maleate salt was prepared by lyophilysis of an equimolar solution of the product and maleic acid in water/dioxan. Found: C 54.67, H 4.69, N 10.07%; $C_{19}H_{19}N_3O_6S$ requires: C 54.67, H 4.59, N 10.07%.

EXAMPLE 2

N-[2-(4(5)-Imidazoyl)ethyl]-benzenesulfonamide

Step a

N-[2-(1-benzenesulfonyl-imidazol-4-yl)ethyl]-benzenesulfonamide

To a suspension of histamine (337 mg, 3.04 mmol) in dried dichloromethane (60 ml) was added triethylamine (1.27 ml, 9.10 mmol) and benzenesulfonyl chloride (775 µl, 6.08 mmol). The mixture was stirred at room temperature for 6 h, the solvent evaporated under reduced pressure and the residue taken up in ethyl acetate (50 ml). The triethylamine hydrochloride was filtered off and the filtrate evaporated under reduced pressure. The residue was crystallised from ethyl acetate/hexane to afford the product as a white solid (1.04 g, 93%).

Step b

To a suspension of the product of step a (1.04 g, 2.82 mmol) in ethanol (115 ml) was added a solution of sodium carbonate (1.20 g, 11.3 mmol) in water (85 ml). The mixture was stirred for 24 h and the ethanol removed under reduced pressure at ambient temperature. The aqueous mixture was extracted with chloroform (6×50 ml), and the combined extracts were washed with brine and dried over anhydrous sodium sulfate. Filtration and evaporation under reduced pressure afforded the title compound as a white solid (567 mg, 80%): $^1$H NMR (300 Hz, $d_6$-DMSO) 7.77(2H, m), 7.60(3H, m), 7.46(1H, s), 6.74(1H, s), 2.94(2H, t), 2.57(2H, t). The maleate salt was prepared by lyophilysis of an equimolar solution of the product and maleic acid in water/dioxan. Found: C 46.65, H 4.74, N 10.95%; $C_{15}H_{17}N_3O_6S.1.0H_2O$ requires: C 46.77, H 4.97, N 10.91%.

EXAMPLE 3

N-[2-(4(5)-Imidazoyl)ethyl]-1-naphthalenesulfonamide

Step a

N-[2-(1-(1-naphthalenesulfonyl)-4-imidazoyl)ethyl]-1-naphthalenesulfonamide

To a suspension of histamine (393 mg, 3.54 mmol) in dried dichloromethane (60 ml) was added triethylamine (1.48 ml, 10.6 mmol) and 1-naphthalenesulfonyl chloride (2.01 g, 8.85 mmol). The mixture was stirred at room temperature for 18 h, the solvent evaporated under reduced pressure and the residue taken up in ethyl acetate (100 ml). The triethylamine hydrochloride was removed by filtration and the filtrate evaporated under reduced pressure. Flash column chromatography (silica, 70% ethyl acetate/hexane) gave the product ($R_f$ 0.35) as a colourless foam (1.32 g, 76%).

Step b

To a solution of the product of step a (1.18 g, 2.41 mmol) in ethanol (100 ml) was added a solution of sodium carbonate (1.02 g, 9.64 mmol) in water (35 ml). The mixture was stirred for 18 h and the insoluble material removed by filtration. The ethanol was evaporated under reduced pressure at ambient temperature. The precipitate thus formed was collected by filtration and dried in vacuo at 50° C. Flash column chromatography (silica, 1% $NH_3$ aq (880)/10% MeOH/$CH_2Cl_2$) afforded the title compound ($R_f$ 0.29) as a white solid (366 mg, 50%): $^1$H NMR (300 Hz, $d_6$-DMSO) 11.70(1H, br s), 8.64(1H, dd), 8.21(1H, d), 8.09(2H, m), 8.03(1H, t), 7.68(3H, m), 7.42(1 H, d), 6.66(1H, s), 2.97(2H, m), 2.55(2H, m). The maleate salt was prepared by lyophilysis of an equimolar solution of the product and maleic acid in water/dioxan. Found: C 53.42, H 4.73, N 9.69%; $C_{19}H_{19}N_3O_6S.0.6H_2O$ requires: C 53.31, H 4.75, N 9.82%.

EXAMPLE 4

N-[2-(4(5)-Imidazoyl)ethyl]-3-cyclohexylpropanesulfonamide

Step a

3-Cyclohexylpropanesulfonyl Chloride

A mixture of 1-chloro-3-cyclohexylpropane (8.00 g, 50 mmol), thiourea (3.80 g, 50 mmol) and sodium iodide (100 mg) in ethanol (40 ml) was heated at reflux for 3 h. The solvent was evaporated under reduced pressure and the residue triturated with diethyl ether. The product was collected by filtration, washed with diethyl ether and air dried to afford a white solid (6.64 g), which was suspended in water (50 ml)/dichloromethane (50 ml). With vigorous stirring chlorine gas was bubbled through the mixture for 30 min, maintaining the temperature below 20° C. The organic layer was separated, washed with ice-cold 10% sodium bisulfite aq. (2×50 ml), saturated sodium hydrogencarbonate aq. (2×50 ml) and water (50 ml), and dried over magnesium sulfate. Filtration and evaporation afforded the product as a colourless oil (3.60 g, 34%).

Step b

To a suspension of histamine (222 mg, 2.00 mmol) in dichloromethane (10 ml) was added triethylamine (278 μl, 2.00 mmol) and a solution of the product of step a (224 mg, 1.00 mmol) in dichloromethane (2 ml) dropwise over 5 min. The mixture was stirred for 18 h and the solvent evaporated under reduced pressure to give a white solid. Flash column chromatography (silica, 1% NH$_3$ aq (880)/10% MeOH/ CH$_2$Cl$_2$) afforded the title compound (R$_f$ 0.25) as a colourless oil (100 mg, 33%): $^1$H NMR (300 Hz, CDCl$_3$) 8.80(1H, br s), 7.52(1H, dd), 6.83(1H, s), 5.80(1H, br s), 3.38(2H, t), 2.93(2H, t), 2.84(2H, t), 1.78(2H, m), 1.65(5H, m), 1.25(6H, m), 0.88(2H, m).

EXAMPLE 5

N-[2-(4(5)-Imidazoyl)ethyl]-(3-(1-adamantyl) propane)sulfonamide 3-(1-Adamantyl)propanesulfonyl chloride (700 mg, 2.50 mmol), prepared by the procedure Example 4 step a, was reacted with histamine (555 mg, 5.00 mmol) according to the method for Example 4 step b. Thus, the title compound was obtained as a colourless foam (340 mg, 39%): $^1$H NMR (300 Hz, CDCl$_3$) 7.55(1H, s), 6.86(1H, s), 5.50(1H, br s), 3.41(2H, t), 2.93(2H, t), 2.86(2H, t), 1.94(3H, s), 1.80–1.59 (8H, m), 1.46(6H, s), 1.12(2H, m). The maleate salt was prepared by lyophilysis of an equimolar solution of the product and maleic acid in water/dioxan. Found: C 55.55, H 7.20, N 8.83%; C$_{22}$H$_{33}$N$_3$O$_6$S.0.5H$_2$O requires: C 55.44, H 7.19, N 8.82%.

EXAMPLE 6

N-[5-(4(5)-Imidazoyl)pentyl]-2-naphthalenesulfonamide

Step a

N-[5-(1-(N',N'-Dimethylsulfamoyl)-imidazol-4-yl) pentyl]-2-naphthalenesulfonamide To a solution of 5-(5-aminopentyl)-1-(N,N-dimethylsulfamoyl)-imidazole[1] (166 mg, 0.64 mmol) and triethylamine (107 μl, 0.77 mmol) in dry dichloromethane (2 ml), cooled in ice under an atmosphere of argon, was added 2-naphthalenesulfonyl chloride (175 mg, 0.77 mmol). The solution was stirred for 45 min at 0° C. and the solvent evaporated. Flash column chromatography (silica; 0.5:5:95 ammonia(880)/methanol/dichloromethane) of the residue afforded the product (R$_f$ 0.76) as a colourless foam (224 mg, 79%).

Step b

A solution of the product from step a (224 mg, 0.50 mmol) in a mixture of ethanol (4 ml) and 1M hydrochloric acid (4 ml) was heated at reflux for 6 h and the solvent removed in vacuo. Flash column chromatography (silica; 0.5:5:95–1:10:90 ammonia(880)/methanol/dichloromethane) of the residue afforded the title compound (R$_f$ 0.26; 1:10:90 ammonia(880)/methanol/dichloromethane) as a colourless foam (138 mg, 81%): 1H NMR (300 Hz, d$_6$-DMSO) 11.74(1H, br s), 8.41 (1H, d), 8.13(2H, t), 8.02(1H, d), 7.80(1H, dd), 7.67(3H, m), 7.44 (1H, s), 6.61(1H, s), 2.79(2H, dd), 2.37(2H, t), 1.40(4H, m), 1.22(2H, dd). Found: C 63.04, H 6.22, N 12.19%; C$_{18}$H$_{21}$N$_3$O$_2$S requires: C 62.95, H 6.16, N 12.23%.

EXAMPLE 7

N-[4-(4(5)-Imidazoyl)butyl]-2-naphthalenesulfonamide

Step a 4-(4-Chlorobutyl)-1-(triphenylmethyl)-imidazole

A solution of 5-(4-chlorobutyl)-2-(tert-butyldimethylsilyl)-1-(N,N-dimethylsulfamoyl)-imidazole[1] (8. 80 g, 23.2 mmol) in a mixture of ethanol (100 ml) and 2M hydrochloric acid (100 ml) was heated at reflux for 2 h. The ethanol was evaporated and the aqueous solution extracted with diethyl ether (2×50 ml). The aqueous layer was evaporated and the residue dissolved in dry dichloromethane (100 ml). Triethylamine (6.50 ml, 46.6 mmol) and triphenylmethyl chloride (7.10 g, 25.5 mmol) were added, the solution stirred for 18 h, washed with water and dried over magnesium sulfate. Filtration and evaporation gave a brown oil. Flash column chromatography (silica; 5% methanol/dichloromethane) of the residue afforded the product as a yellow oil (7.20 g, 77%).

Step b 4-(4-Phthalimidobutyl)-1-(triphenylmethyl)-imidazole

Potassium phthalimide (1.67 g, 9.00 mmol) was added to a solution of the product from step b (7.20 g, 18.0 mmol) in dry N,N-dimethylformamide (50 ml), under an atmosphere of argon. The mixture was stirred and heated at 100° C. for 5 h, allowed to cool to room temperature and poured onto ice/water (150 ml). The resultant white precipitate was collected by filtration. The residue was dissolved in dichloromethane (100 ml), washed brine and dried over magnesium sulfate. The solvent was evaporated and the residue purified by flash column chromatography (silica; 5% methanol/dichloromethane), from which the product was isolated as a yellow oil (4–50 g, 98%).

Step c 4-(4-Aminobutyl)-1-(triphenylmethyl)-imidazole

To a suspension of the product from step 8 (3.00 g, 5.86 mmol) in ethanol (30 ml) was added hydrazine hydrate (1.5 ml, 25.8 mmol). The mixture was heated at reflux for 2 h and allowed to cool to room temperature. The preciptate was removed by filtration. The filtrate was evaporated and the residue triturated with chloroform. The solid material was again removed by filtration. The filtrate was evaporated and the trituration process repeated to give the product as a yellow oil (2.05 g, 92%).

Step d

N-[4-(1-(Triphenylmethyl)-imidazol-4-yl)butyl]-2-naphthalenesulfonamide

To a solution of the product from step c (465 mg, 1.22 mmol) and triethylamine (185 μl, 1.33 mmol) in dry dichloromethane (15 ml) was added 2-naphthalenesulfonyl chloride (227 mg, 1.22 mmol). The solution was stirred for 2 h and the solvent evaporated. Flash column chromatography (silica; 5% methanol/dichloromethane) of the residue afforded the product as a colourless foam (588 mg, 84%).

Step e

A solution of the product from step d (588 mg, 1.02 mmol) in trifluoroacetic acid (5 ml) was stirred for 18 h and the solvent evaporated. Flash column chromatography (silica; 1:10:90 ammonia(880)/methanol/dichloromethane) of the residue afforded the title compound (R$_f$ 0.24) as a white solid (96 mg, 63%): $^1$H NMR (300 Hz, d$_6$-DMSO) 11.70(1H, br s), 8.41 (1H, s), 8.13(2H, t), 8.03(1H, d), 7.80(1H, dd), 7.67(3H, m), 7.45(1H, s), 6.62(1H, s), 2.76 (2H, dd), 2.38(2H, t), 1.48(2H, m), 1.41(2H, dd). The maleate salt was prepared by lyophilysis of an equimolar solution of the product and maleic acid in water/dioxan. Found: C 56.55, H 5.31, N 9.31%; C$_{21}$H$_{23}$N$_3$O$_6$S.0.5H$_2$O requires: C 56.62, H 5.20, N 9.43%.

EXAMPLE 8

N-[6-(4(5)-Imidazoyl)hexyl-2-naphthalenesulfonamide

The title compound was prepared according to the procedure for Example 6, using 5-(6-aminohexyl)-1-(N,N-dimethylsulfamoyl)-imidazole[1] as the substrate in step a. The product of the two steps was obtained as white solid: 1H NMR (300 Hz, d$_6$-DMSO) 11.72(1H, br s), 8.41 (1H, d), 8.13(2H, dd), 8.03(1H, d), 7.80(1H, dd), 7.67(3H, m), 7.44(1H, s), 6.62(1H, s), 2.74(2H, dd), 2.37(2H, t), 1.42(2H, m), 1.33(2H, m), 1.17(4H, m). Found: C 60.99, H 6.59, N 11.17%; Cl$_9$H23N$_3$O$_2$S.0.9H$_2$O requires: C 61.07, H 6.69, N 11.24%.

EXAMPLE 9

N-[5-(4(5)-Imidazoyl)pentyl]-(4-chlorophenyl)methanesulfonamide

Step a

N-[5-(1-(N',N'-Dimethylsulfamoyl)-imidazol-4-yl)pentyl]-(4-chlorophenyl)methanesulfonamide To a solution of S-(5-aminopentyl)-1-(N,N-dimethylsulfamoyl)imidazole[1] (412 mg, 1.58 mmol) and triethylamine (264 μl, 1.90 mmol) in dry dichloromethane (5 ml), cooled under an atmosphere of argon to −78° C., was added dropwise a solution of (4-chlorophenyl) methanesulfonyl chloride (533 mg, 2.37 mmol) in dry dichloromethane (5 ml). The resultant solution was stirred for 18 h, allowing to warm to room temperature, and the solvent evaporated. Flash column chromatography (silica; 0.5:5:95 ammonia(880)/methanol/dichloromethane) of the residue afforded the product (R$_f$ 0.66; 1:10:90 ammonia (880)/methanol/dichloromethane) as a colourless oil (307 mg, 43%).

Step b

A solution of the product from step a (275 mg, 0.61 mmol) in a mixture of ethanol (4 ml) and 1M hydrochloric acid (4 ml) was heated at reflux for 18 h and the solvent removed in vacuo. Flash column chromatography (silica; 1:10:90 ammonia(880)/methanol/dichloromethane) of the residue afforded the product (R$_f$ 0.34; 1:10:90 ammonia(880)/methanol/dichloromethane) as a white crystalline solid (181 mg, 87%): $^1$H NMR (300 Hz, d$_6$-DMSO) 11.75(1H, br s), 7.46(1H, s), 7.43(2H, dd), 7.37(2H, d), 7.04(1H, t), 6.68(1H, s), 4.31(2H, s), 2.87(2H, dd), 2.45(2H, t), 1.50(2H, m), 1.40(2H, m), 1.27(2H, m). Found: C 52.88, H 6.13, N 12.28%; C$_{15}$H$_{20}$ClN$_3$O$_2$S requires: C 52.70, H 5.90, N 12.29%.

EXAMPLE 10

N-[4-(4(5)-Imidazoyl)butyl]-(4-chlorophenyl)methanesulfonamide

The title compound was prepared according to the procedure for Example 9, using 4-(4-aminobutyl)-1-(triphenylmethyl)-imidazole (Example 7 step c) as the substrate in step a. The product of the two steps was obtained as white solid: $^1$H NMR (300 Hz, d$_6$-DMSO) 7.47(1H, s), 7.43(2H, dd), 7.37(2H, d), 7.05(1H, t), 6.69(1H, s), 4.31(2H, s), 2.89(2H, dd), 2.46(2H, t), 1.55(2H, m), 1.45(2H, m). The maleate salt was prepared by lyophilysis of an equimolar solution of the product and maleic acid in water/dioxan. Found: C 48.68, H 5.14, N 9.32%; C$_{18}$H$_{22}$ClN$_3$O$_6$S requires: C 48.70, H 5.00, N 9.47%.

EXAMPLE 11

N-[6-(4(5)-Imidazoyl)hexyl]-(4-chlorophenyl)methanesulfonamide

The title compound was prepared according to the procedure for Example 9, using 5-(6-aminohexyl)-1-(N,N-dimethylsulfamoyl)-imidazole as the substrate in step a. The product of the two steps was obtained as a white crystalline solid: $^1$H NMR (300 Hz, d$_6$-DMSO) 11.71(1H, br s), 7.46 (1H, s), 7.43(2H, ddd), 7.37(2H, ddd), 7.05(1H, t), 6.68(1H, s), 4.31(2H, s), 2.86(2H, dd), 2.46(2H, t), 1.52(2H, m), 1.37(2H, m), 1.27(4H, m). Found: C 51.51, H 6.28, N 15.05%; C$_{16}$H$_{22}$ClN$_3$O$_2$S requires: C 51.81, H 6.25, N 15.11%.

EXAMPLE 12

N-[5-(4(5)-Imidazoyl)pentyl]-N'-(4-chlorophenyl)methyl-sulfamide

Step a

N-[5-(1-(N", N"-Dimethylsulfamoyl)-imidazol-4-yl)pentyl]-N'-tert-butoxycarbonyl-sulfamide To a solution of chlorosulfonyl isocyanate (211 μl, 2.42 mmol) in dry dichloromethane (3 ml), cooled in ice under an atmosphere of argon, was added dropwise a solution of dry t-butanol (346 μl, 3.63 mmol) in dry dichloromethane (3 ml). The solution was allowed to warm to room temperature, stirred for 10 min and added dropwise, under argon, to an ice-cooled solution of 5-(5-aminopentyl)-1-(N,N-dimethylsulfamoyl)-imidazole[1] (484 mg, 1.86 mmol) and triethylamine (388 μl, 2.79 mmol) in dry dichloromethane (6 ml). The mixture was stirred for 18 h, allowing to warm to room temperature, and the solvent evaporated. Flash column chromatography (silica; 0.5:5:95 ammonia(880)/methanol/dichloromethane) of the residue afforded the product (R$_f$ 0.29; 1:10:90 ammonia(880)/methanol/dichloromethane) as a colourless oil (400 mg, 49%).

Step b

N'-(4-Chlorophenyl)methyl-N-[5-(1(N",N"-dimethylsulfamoyl)-imidazol-4-yl)pentyl]-N'-tert-butoxycarbonyl-sulfamide To a solution of the product from step a (390 mg, 0.89 mmol) and 4-chlorobenzyl bromide (183 mg, 0.89 mmol) in dry N,N-dimethylformamide (3 ml), cooled under an atmosphere of argon to −15° C., was added sodium hydride (36 mg, 0.89 mmol, 60% dispersion in oil). The mixture was stirred for 18 h, allowing to warm slowly to ambient temperature. Water (15 ml) was added and the mixture was extracted with ethyl acetate (4×10 ml). The combined organics were washed four times with water, dried over sodium sulfate and evaporated. Flash column chromatography (silica; 0.2:2:98 ammonia(880)/methanol/dichloromethane) of the residue afforded the product (R$_f$ 0.29; 1:10:90 ammonia(880)/methanol/dichloromethane) as a colourless oil (378 mg, 75%).

Step c

A suspension of the product from step b (374 mg, 0.66 mmol) in a mixture of ethanol (5 ml) and 1M hydrochloric acid (5 ml) was heated at reflux for 18 h and the solvent removed in vacuo. Flash column chromatography (silica; 1:10:90 ammonia(880)/methanol/dichloromethane) of the residue afforded the product ($R_f$ 0.24) as a white solid (132 mg, 56%): $^1$H NMR (300 Hz, $d_6$-DMSO) 7.46(1H, s), 7.43(5H, m), 6.87(1H, t), 6.68(1H, s), 4.03(2H, d), 2.78(2H, dd), 2.45(2H, t), 1.58(2H, m), 1.47(2H, m), 1.27(2H, m). Found: C 50.33 H 5.88, N 15.55%; $C_{15}H_{21}ClN_4O_2S$ requires: C 50.48, H 5.93, N 15.70%.

EXAMPLE 13

N-[4-(4(5)-Imidazoyl)butyl]-N'-(4-chlorophenyl) methyl-sulfamide

The title compound was prepared according to the procedure for Example 12, using 4-(4-aminobutyl)-1-(triphenylmethyl)-imidazole (Example 7 step c) as the substrate in step a. The product of the three steps was obtained as white solid: $^1$H NMR (300 Hz, $d_6$-DMSO) 11.68(1H, br s), 7.47(1H, d), 7.36(4H, m), 6.86(1H, t), 6.68(1H, s), 3.98(2H, d), 2.79(2H, dd), 2.45(2H, t), 1.53(2H, m), 1.43 (2H, m). Found: C 49.08 H 5.61, N 16.23%; $C_{14}H_{19}ClN_4O_2S$ requires: C 49.05, H 5.59, N 16.34%.

EXAMPLE 14

N-[3-(4(5)-Imidazoyl)propyl]-N'-(4-chlorophenyl) methyl-sulfamide

Step a 4-(3-Phthalimidopropyl)-1-(triphenylmethyl)-imidazole

To a solution of 3-[1-(triphenylmethyl)imidazol-4-yl] propan-1-ol (2.24 g, 6.07 mmol) in dry tetrahydrofuran (10 ml), under an argon atmosphere, was added phthalimide (1.16 g, 7.89 mmol) and triphenylphosphine (2.07 g, 7.89 mmol). The suspension was cooled in ice and a solution of diethylazodicarboxylate (1.24 ml, 7.89 mmol) in dry tetrahydrofuran (10 ml) was added dropwise. The mixture was allowed to warm to room temperature and stirred for 2h. Diethyl ether (20 ml) was added. The precipitate was collected by filtration and dried in vacuo to afford a white solid (2.08 g, 68%).

Step b 4-(3-Aminopropyl)-1-(triphenylmethyl)-imidazole

To a suspension of the product from step a (4.09 g, 8.22 mmol) in ethanol (82 ml) was added hydrazine hydrate (2.32 ml, 41.1 mmol). The mixture was heated at reflux for 3 h and allowed to cool to room temperature. The preciptate was removed by filtration. The filtrate was evaporated and the residue triturated with chloroform. The solid material was again removed by filtration. The filtrate was evaporated and the trituration process repeated to give the product as a yellow oil in quantitative yield.

Step c

N-[3-(1-(triphenylmethyl)-imidazol-4-yl)propyl]-N'-tert-butoxycarbonyl-N'-(4-chlorophenyl)methyl-sulfamide The product from step b was converted to the product according to the procedure of Example 12 steps a and b.

Step d

A solution of the product from step c (308 mg, 0.46 mmol) in trifluoroacetic acid (3 ml) was stirred for 18 h and the solvent evaporated. Flash column chromatography (silica; 1:10:90 ammonia(880)/methanol/dichloromethane) of the residue afforded the title compound ($R_f$ 0.18) as a white solid (96 mg, 63%): $^1$H NMR (300 Hz, $d_6$-DMSO) 11.77(1H, br s), 7.37(4H, m), 6.99(1H, t), 6.72(1H, s), 3.98(2H, d), 2.81(2H, dd), 2.48(2H, m), 1.72(2H, m). Found: C 47.30, H 5.26, N 16.95%; $C_{13}H_{17}ClN_4O_2S$ requires: C 47.49, H 5.21, N 17.04%.

EXAMPLE 15

N-[6-(4(5)-Imidazoyl)hexyl]-N'-(4-chlorophenyl) methyl-sulfamide

The title compound was prepared according to the procedure for Example 12, using 5-(6-aminohexyl)-1-(N,N-dimethylsulfamoyl)-imidazole as the substrate in step a. The product of the three steps was obtained as a white solid: $^1$H NMR (300 Hz, $d_6$-DMSO) 7.46(1H, d), 7.35(5H, m), 6.86 (1H, t), 6.67(1H, s), 3.98(2H, d), 2.75(2H, dd), 2.45(2H, t), 1.52(2H, m), 1.38(2H, m), 1.25(4H, m). Found: C 51.51, H6.28, N 15.05%; $C_{16}H_{23}ClN_4O_2S$ requires: C 51.81, H 6.25, N 15.11%.

EXAMPLE 16

N-[2-(4(5)-Imidazoyl)ethyl]-3,4-dichlorobenzenesulfonamide

The title compound was prepared according to the procedure for Example 2, using histamine and 3,4-dichlorobenzenesulfonyl chloride (prepared essentially as Example 4 step a) as the substrates in step a. The product of the two steps was obtained as a white crystalline solid: $^1$H NMR (300 Hz, $d_6$-DMSO) 11.80(1H, br s), 7.94(1H, d), 7.90(1H, m), 7.87(1H, m), 7.72(1H, dd), 7.47(1H, s), 6.76 (1H, s), 3.00(2H, t), 2.59(2H, t).

EXAMPLE 17

N-[2-(4(5)-Imidazoyl)ethyl]-2-phenylethanesulfonamide

Step a 4-(2-Phthalimidoethyl)-1-(triphenylmethyl)-imidazole

To a suspension of 4(5)-(2-phthalimidoethyl)-imidazole[2] (838 mg, 3.48 mmol) in dry dichloromethane (10 ml), under an argon atmosphere, was added triethylamine (728 μl, 5.22 mmol) and triphenylmethyl chloride (1.16 g, 4.18 mmol). Flash column chromatography (silica; 0.2:2:98 to 1:10:90 ammonia(880)/methanol/dichloromethane) of the residue afforded the product as a foam (1.20 g, 71%).

Step b 4-(2-Aminoethyl)-1-(triphenylmethyl)-imidazole

To a suspension of the product from step a (1.20 g, 2.48 mmol) in ethanol (25 ml) was added hydrazine hydrate (702 ml, 12.4 mmol). The mixture was heated at reflux for 90min and allowed to cool to room temperature. The preciptate was removed by filtration. The filtrate was evaporated and the residue triturated with chloroform. The solid material was again removed by filtration. The filtrate was evaporated and the trituration process repeated to give the product as a yellow oil (818 mg, 93%).

Step c

N-[2-(1-(Triphenylmethyl)imidazoyl-4-yl))ethyl]-2-phenylethanesulfonamide

To a solution of the product from step b (353 mg, 1.00 mmol) and triethylamine (154 μl, 1.10 mmol) in dry dichloromethane (5 ml) was added a solution of 2-phenylethanesulfonyl chloride (prepared essentially as Example 4 step a) (205 mg, 1.00 mmol) in dry dichloromethane (2 ml). The solution was stirred for 30min, washed with water and dried over magnesium sulfate. Filtration and evaporation afforded the product ($R_f$ 0.68; 1:10:90 ammonia(880)/methanol/dichloromethane) as a white solid (450 mg, 86%).

Step d

A solution of the product from step c (440 mg, 0.84mmol) in trifluoroacetic acid (4 ml) was stirred for 18 h and the solvent evaporated. Flash column chromatography (silica; 1:10:90 ammonia(880)/methanol/dichloromethane) of the residue afforded the title compound ($R_f$ 0.25) as an oil (61 mg, 26%): $^1$H NMR (300 Hz, CDCl$_3$) 7.83(1H, s), 7.20(5H, m), 6.93(1H, s), 3.39(2H, m), 3.27(2H, m), 3.08(2H, m), 2.88(2H, m). The maleate salt was prepared by lyophilysis of an equimolar solution of the product and maleic acid in water/dioxan. Found: C 51.35, H 5.41, N 10.62%; C$_{17}$H$_{21}$N$_3$O$_6$S requires: C 51.64, H 5.35, N 10.63%.

EXAMPLE 18

N-[2-(4(5)-Imidazoyl)ethyl]-3-phenylpropanesulfonamide

The title compound was prepared according to the procedure for Example 17, using 3-phenylpropanesulfonyl chloride (prepared essentially as Example 4 step a) as the substrate in step c. The product ($R_f$ 0.26; 1:10:90 ammonia (880)/methanol/dichloromethane) of the four steps was obtained as a colourless oil: $^1$H NMR (300 Hz, CDCl$_3$) 9.80(1H br s), 7.50(1H, s), 7.42(2H, t), 7.20(1H, m), 7.13 (2H, m), 6.80(1H, s), 3.30(2H, t), 2.95(2H, t), 2.79(2H, t), 2.70(2H, t), 2.07(2H, quint.). The maleic acid salt was prepared by lyophilysis of an equimolar solution of the product and maleic acid in water/dioxan. Found: C 52.69, H 5.71, N 10.23%; C$_{18}$H$_{23}$N$_3$O$_6$S requires: C 52.80, H 5.66, N 10.27%.

EXAMPLE 19

N-[2-(4(5)-Imidazoyl)ethyl]-2-naphthylmethanesulfonamide

The title compound was prepared according to the procedure for Example 17, using 2-naphthylmethanesulfonyl chloride (prepared essentially as Example 4 step a) as the substrate in step c. The product ($R_f$ 0.27; 1:10:90 ammonia (880)/methanol/dichloromethane) of the four steps was obtained as a white solid: H NMR (300 Hz, d$_6$-DMSO) 11.75(1H br s), 7.89(4H, m), 7.51(4H, m), 7.17(1H, t), 6.79(1H, s), 4.46(2H, s), 3.17(2H, dd), 2.66(2H, m). The maleic acid salt was prepared by lyophilysis of an equimolar solution of the product and maleic acid in water/dioxan. Found: C 54.30, H 5.09, N 9.55%; C$_{20}$H$_{21}$N$_3$O$_6$S.0.5H$_2$O requires: C 54.33, H 5.03, N 9.53%.

EXAMPLE 20

(E)-N-[2-(4(5)-Imidazoyl)ethyl]-2-phenylethenesulfonamide

The title compound was prepared according to the procedure for Example 17, using trans-β-styrenesulfonyl chloride as the substrate in step c. The product ($R_f$ 0.13; 1:10:90 ammonia(880)/methanol/dichloromethane) of the four steps was obtained as a colourless foam: $^1$H NMR (300 Hz, CDCl$_3$) 7.56(1H, d), 7.42(6H, m), 6.84(1H, s), 6.73(1H, d), 3.36(2H, t), 2.86(2H, t). Found: C 54.41, H 5.49, N 14.69%; C$_{13}$H$_{15}$N$_3$O$_2$S.0.5H$_2$O requires: C 54.53, H 5.63, N 14.67%.

EXAMPLE 21

N-[2-(4(5)-Imidazoyl)ethyl]-phenylmethanesulfonamide

The title compound was prepared according to the procedure for Example 9, using phenylmethanesulfonyl chloride as the substrate in step c. The product ($R_f$ 0.27; 1:10:90 ammonia(880)/methanol/dichloromethane) of the four steps was obtained as a white solid: $^1$H NMR (300 Hz, d$_6$-DMSO) 7.50(1H, s), 7.31(5H, m), 7.20(1H, t), 6.80(1H, s), 4.27(2H, s), 3.13(2H, m), 2.63(2H, t). Found: C 54.39, H 5.73, N 15.60%; C$_{12}$H$_{15}$N$_3$O$_2$S requires: C 54.32, H 5.70, N 15.84%.

EXAMPLE 22

N-[2-(4(5)-Imidazoyl)ethyl]-8-quinolinesulfonamide

The title compound was prepared according to the procedure for Example 17, using 8-quinolinesulfonyl chloride as the substrate in step c. The product ($R_f$ 0.34; 1:10:90 ammonia(880)/methanol/dichloromethane) of the four steps was obtained as a colourless crystalline solid: $^1$H NMR (300 Hz, CDCl$_3$) 8.82(1H, dd), 8.42(1H, dd), 8.25(1H, dd), 8.05(1H, d), 7.64(1H, dd), 7.51(1H, dd), 7.38(1H, d), 6.66 (1H, d), 3.17(2H, t), 2.74(2H, t). Found: C 55.33, H 4.81, N 18.47%; C$_{14}$H$_{14}$N$_4$O$_2$S requires: C 55.61, H 4.67, N 18.53%.

EXAMPLE 23

N-[2-(4(5)-Imidazoyl)ethyl]-2-cyclohexylethanesulfonamide

The title compound was prepared according to the procedure for Example 17, using 2-cyclohexylethanesulfonyl chloride (prepared essentially as Example 4 step a) as the substrate in step c. The product ($R_f$ 0.27; 1:10:90 ammonia (880)/methanol/dichloromethane) of the four steps was obtained as a white solid: $^1$H NMR (300 Hz, d$_6$-DMSO) 11.80(1H br s), 7.51(1H, s), 7.05(1H, t), 6.81(1H, s), 3.13 (2H, dd), 2.90(2H, m), 2.65(2H, t), 1.62(5H, m), 1.47(2H, m), 1.16(4H, m), 0.86(2H, m). Found: C 54.68, H 8.20, N 14.71%; Cl$_3$H$_{23}$N$_3$O$_2$S requires: C 54.70, H 8.12, N 14.72%.

EXAMPLE 24

N-[2-(4(5)-Imidazoyl)ethyl]-(3,4-dichlorophenyl) methanesulfonamide

The title compound was prepared according to the procedure for Example 9, using (3,4-dichlorophenyl) methanesulfonyl chloride (prepared essentially as Example 4 step a) as the substrate in step a. The product ($R_f$ 0.31; 1:10:90 ammonia(880)/methanol/dichloromethane) of the four steps was obtained as a white solid: $^1$H NMR (300 Hz, d$_6$-DMSO) 11.85(1H br s), 7.60(3H, m), 7.32(1H, dd), 7.23(1H, t), 6.82(1H, s), 4.36(2H, s), 3.16(2H, dd), 2.65(2H, t). Found: C 42.79, H 3.98, N 12.49%; C$_{12}$H$_{13}$Cl$_2$N$_3$O$_2$S requires: C 43.12, H 3.92, N 12.57%.

EXAMPLE 25

N-[2-(4(5)-Imidazoyl)ethyl]-(4-chlorophenyl) methanesulfonamide

The title compound was prepared according to the procedure for Example 9, using (4-chlorophenyl)

methanesulfonyl chloride (prepared essentially as Example 4 step a) as the substrate in step a. The product (R$_f$ 0.19; 1:10:90 ammonia(880)/methanol/dichloromethane) of the four steps was obtained as a white solid: $^1$H NMR (300 Hz, d$_6$-DMSO) 7.54(1H, d), 7.43(2H, d), 7.34(2H, d), 7.16(1H, t), 6.82(1H, s), 4.31(2H, s), 3.14(2H, dd), 2.65(2H, t). Found: C 48.01, H 4.80, N 14.14%; C$_{12}$H$_{14}$ClN$_3$O$_2$S requires: C 48.08, H 4.71, N 14.02%.

EXAMPLE 26

N-[3-(4(5)-Imidazoyl)propyl]-(4-chlorophenyl)methanesulfonamide

Step a

N-[3-(1-(triphenylmethyl)imidazoyl-4-yl)propyl]-(4-chlorophenyl)methanesulfonamide 4-(3-Aminopropyl)-1-(triphenylmethyl)-imidazole (Example 14 step b) (593 mg, 1.61 mmol) was reacted with (4-chlorophenyl)methanesulfonyl chloride (prepared essentially as Example 4 step a) (545 mg, 2.42 mmol) in the presence of triethylamine (270 μl, 1.94 mmol) according to the procedure of step a Example 9. Thus, the product was isolated as a colourless foam (489 mg, 62%).

Step b

The product from step a was deprotected according to the procedure of step d Example 17 and the title compound (R$_f$ 0.17; 1:10:90 ammonia(880)/methanol/dichloromethane) was isolated in quantative yield as a white solid: 1H NMR (300 Hz, d$_6$-DMSO) 11.77(1H, br s), 7.50(1H, s), 7.43(2H, d), 7.37(2H, d), 7.14(1H, t), 6.72(1H, s), 4.32(2H, s), 2.92 (2H, dd), 2.46(2H, t), 1.70(2H, m). Found: C 49.54, H 5.38, N 13.12%; C$_{13}$H$_{16}$ClN$_3$O$_2$S requires: C 49.76, H 5.14, N 13.39%.

EXAMPLE 27

N-[3-(4(5)-Imidazoyl)propyl]-benzenesulfonamide

The title compound was prepared according to the procedure for Example 26, using benzenesulfonyl chloride as the substrate in step a. The product (R$_f$ 0.16; 1:10:90 ammonia(880)/methanol/dichloromethane) of the four steps was obtained as a white solid: H NMR (300 Hz, CDCl$_3$) 7.86(2H, d), 7.54(4H, m), 6.76(1H, s), 3.04(2H, t), 2.67(2H, t), 1.81(2H, quint.). FAB M/S: [M$^+$+H] 266; Accurate mass: 266.0936; C$_{12}$H$_{16}$N$_3$O$_2$S requires: 266.0963. The maleate salt was prepared by lyophilysis of an equimolar solution of the product and maleic acid in water/dioxan.

EXAMPLE 28

N-[3-(4(5)-Imidazoyl)propyl]-2-naphthalenesulfonamide

The title compound was prepared according to the procedure for Example 26, using 2-naphthalenesulfonyl chloride as the substrate in step a. The product (R$_f$ 0.17; 1:10:90 ammonia(880)/methanol/dichloromethane) of the four steps was obtained as a white solid: $^1$H NMR (300 Hz, d$_6$-DMSO) 8.40(1H, s), 8.10(2H, t), 8.02(1H, d), 7.74(4H, m), 7.44(1H, s), 6.62(1H, s), 2.78(2H, dd), 2.43(2H, t), 1.62(2H, quint.). Found: C 60.69, H 5.51, N 13.18%; C$_{16}$H$_{17}$N$_3$O$_2$S requires: C 60.93, H 5.43 N 13.32%.

EXAMPLE 29

N-7-(4(5)-Imidazoyl)heptyl]-2-naphthalenesulfonamide

Step a

2-(tert-Butyldimethylsilyl)-1-(N,N-dimethylsulfamoyl)-imidazole

A solution of 1-(N,N-dimethylsulfamoyl)-imidazole$^1$ (4.48 g, 25.6 mmol) in dry tetrahydrofuran (100 ml) was cooled under an atmosphere of argon to −78° C. n-Butyl lithium (1.5M in hexanes) (18.0 ml, 27.0 mmol) was added over 30min and the solution stirred for a further 30min. To the resulting brown solution was added over 15 min a solution of tert-butyldimethylsilyl chloride in dry tetrahydrofuran (20 ml). The solution was allowed to warm to room temperature and stirred for 24h. Saturated ammonium chloride solution (100 ml) and diethyl ether (100 ml) were added and the ethereal extract was washed with brine and dried over magnesium sulfate. Filtration and evaporation of the filtrate gave an oily residue, which was purified by flash column chromatography (silica; ethyl acetate) to afford the product as an amber solid (6.97 g, 94%).

Step b

5-(7-Bromoheptyl)-2-(tert-butyldimethylsilyl)-1-(N,N-dimethylsulfamoyl)imidazole A solution of the product from step a (2.50 g, 8.64 mmol) in dry tetrahydrofuran (30 ml) was cooled under an atmosphere of argon to −78° C. n-Butyl lithium (1.5M in hexanes) (8.50 ml, 12.7 mmol) was added over 15 min and the solution stirred for a further 30 min. A solution of 1,7-dibromoheptane (4.60 g, 17.3 mmol) in dry tetrahydrofuran (6 ml) was added over 10 min. The solution was stirred for 30min, allowed to warm to room temperature and stirred for 18 h. Saturated ammonium chloride solution (50 ml) and ethyl acetate (50 ml) were added and the organic extract was washed with brine and dried over sodium sulfate. Filtration, evaporation of the filtrate and purification by flash column chromatography (silica; 20% ethyl acetate/hexane) afforded the product (R$_f$ 0.55) as a white solid (2.48 g, 62%).

Step c

1-(N,N-Dimethylsulfamoyl)-5-(7-phthalimidoheptyl)-imidazole

Potassium phthalimide (1.67 g, 9.00 mmol) was added to a solution of the product from step b (2.10 g, 4.50 mmol) in dry N,N-dimethylformamide (10 ml), under an atmosphere of argon. The mixture was stirred and heated at 100° C. for 18 h and allowed to cool to room temperature. Water (75 ml) was added and the mixture extracted with dichloromethane (3×40 ml). The combined extracts were evaporated, the residue dissolved in ethyl acetate (75 ml) and the solution washed five times with brine. The solvent was evaporated and the residue purified by flash column chromatography (silica; ethyl acetate), from which the product was isolated as a yellow oil (1.75 g, 93%).

Step d

5-(7-Aminoheptyl)-1-(N,N-dimethylsulfamoyl)-imidazole

The product from step c was deprotected according to the procedure of Example 17 step b.

Step e

The title compound was prepared according to the procedure for Example 6, using 5-(7-aminoheptyl)-1-(N,N- dimethylsulfamoyl)-imidazole as the substrate in step a. The product ($R_f$ 0.38; 1:10:90 ammonia(880)/methanol/dichloromethane) of the two steps was obtained as a white solid: $^1$H NMR (300 Hz, $d_6$-DMSO) 8.41 (1H, s), 8.13(2H, dd), 8.02(1H, dd), 7.80(1H, dd), 7.67(3H, m), 7.45(1H, d), 6.64(1H, s), 2.75(2H, dd), 2.38(2H, t), 1.43(2H, m), 1.32 (2H, m), 1.13(6H, m).

EXAMPLE 30

N-[8-(4(5)-Imidazoyl)octyl]-2-naphthalenesulfonamide

The title compound was prepared according to the procedure for Example 6, using 5-(8-aminooctyl)-1-(N,N-dimethylsulfamoyl)-imidazole[1] as the substrate in step a. The product ($R_f$ 0.39; 1:10:90 ammonia(880)/methanol/dichloromethane) of the two steps was obtained as a white solid: $^1$H NMR (300 Hz, $d_6$-DMSO) 11.72(1H, br s), 8.40 (1H, d), 8.13(2H, dd), 8.02(1H, dd), 7.80(1H, dd), 7.65(3H, m), 7.45(1H, d), 6.65(1H, d), 2.75(2H, dd), 2.41(2H, t), 1.45(2H, quint.), 1.32(2H, quint.), 1.12(8H, m).

EXAMPLE 31

N-[10-(4(5)-Imidazoyl)decyl]-2-naphthalenesulfonamide

The title compound was prepared according to the procedure for Example 6, using 5-(10-aminodecyl)-1-(N,N-dimethylsulfamoyl)-imidazole[1] as the substrate in step a. The product ($R_f$ 0.33; 1:10:90 ammonia(880)/methanol/dichloromethane) of the two steps was obtained as a white solid: 1H NMR (300 Hz, $d_6$-DMSO) 8.40 (1H, d), 8.12(2H, dd), 8.02(1H, dd), 7.80(1H, dd), 7.66(3H, m), 7.46(1I, d), 6.66(1H, s), 2.75(2H, dd), 2.44(2H, t), 1.47(2H, m), 1.31 (2H, m), 1.10(12H, m).

EXAMPLE 32

N-[7-(4(5)-Imidazoyl)heptyl]-(4-chlorophenyl)methanesulfonamide

The title compound was prepared according to the procedure for Example 9, using 5-(7-aminoheptyl)-1-(N,N-dimethylsulfamoyl)-imidazole (Example 29 step d) as the substrate in step a. The product ($R_f$ 0.30; 1:10:90 ammonia (880)/methanol/dichloromethane) of the two steps was obtained as a white solid: $^1$H NMR (300 Hz, $d_6$-DMSO) 7.56(1H, s), 7.42(2H, d), 7.37(2H, d), 7.04(1H, t), 6.72(1H, s), 4.30(2H, s), 2.85(2H, dd), 2.48(2H, m), 1.53(2H, m), 1.37(2H, m), 1.24(6H, m).

EXAMPLE 33

N-[8-(4(5)-Imidazoyl)octyl]-(4-chlorophenyl)methanesulfonamide

Step a 5-(8-Bromooctyl)-2-(tert-butyldimethylsilyl)-1-(N,N-dimethylsulfamoyl)imidazole A solution of 2-(tert-butyldimethylsilyl)-1-(N,N-dimethylsulfamoyl) imidazole (Example 29 step a) (2.62 g, 9.05 mmol) in dry tetrahydrofuran (30 ml) was cooled under an atmosphere of argon to −78° C. n-Butyl lithium (1.5M in hexanes) (7.25 ml, 10.9 mmol) was added over 15 min and the solution stirred for a further 30 min. A solution of 1,8-dibromooctane (2.55 ml 13.6 mmol) in dry tetrahydrofuran (5 ml) was added over 10 min. The solution was stirred for 2 h, allowed to warm to room temperature and stirred for 18 h. Saturated ammonium chloride solution (30 ml) and diethyl ether (30 ml) were added and the ethereal extract was washed with brine and dried over sodium sulfate. Filtration, evaporation of the filtrate and purification by flash column chromatography (silica; 20%; ethyl acetate/hexane) to afford the product ($R_f$ 0.43) as a white solid (2.36 g, 54%).

Step b 2-(tert-Butyldimethylsilyl)-1-(N,N-dimethylsulfamoyl)-5-(8-phthalimidooctyl)imidazole (A) and 1-(N,N-dimethylsulfamoyl)-5-(8-phthalimidooctyl)-imidazole (B)

Potassium phthalimide (1.84 g, 9.95 mmol) was added to a solution of the product of step a (2.39 g, 4.97 mmol) in dry dimethyl formamide (16 ml), under an atmosphere of argon. The mixture was stirred and heated at 100° C. for 18 h and allowed to cool to room temperature. Water (80 ml) was added and the mixture extracted with dichloromethane (3×40 ml). The combined extracts were evaporated, the residue dissolved in ethyl acetate (80 ml) and the solution washed four times with brine. The solvent was evaporated and the residue purified by flash column chromatography (silica; ethyl acetate), from which compound (A) ($R_f$ 0.72) was isolated as an amber oil (639 mg, 23%) and compound (B) ($R_f$ 0.27) as an oily solid (1.56 g, 73%).

Step c 5-(8-Aminooctyl)-2-(tert-butyldimethylsilyl)J-1-N,N-dimethylsulfamoyl) imidazole Compound A from step b was deprotected according to the procedure of Example 17 step b.

Step d

The title compound was prepared according to the procedure for Example 9, using 5-(8-aminooctyl)-2-(tert-butyldimethylsilyl)-1-(N,N-dimethylsulfamoyl)imidazole, the product of the previous reaction, as the substrate in step a. The product ($R_f$ 0.42; 1:10:90 ammonia(880)/methanol/dichloromethane) was obtained as a white solid: $^1$H NMR (300 Hz, $d_6$-DMSO) 7.47(1H, d), 7.43(2H, d), 7.36(2H, d), 7.03(1H, t), 6.68(1H, s), 4.30(2H, s), 2.85(2H, dd), 2.46(2H, t), 1.53(2H, m), 1.37(2H, m), 1.23(8H, m). Found C 55.99, H 7.04, N 10.67%. $C_{18}H_{26}ClN_3O_2S$ requires C 56.31, H 6.83, N 10.94%

EXAMPLE 34

N-[10-(4(5)-Imidazoyl)decyl]-(4-chlorophenyl)methanesulfonamide

The title compound was prepared according to the procedure for Example 9, using 5-(10-aminodecyl)-1-(N,N-dimethylsulfamoyl)-imidazole[1] as the substrate in step a. The product ($R_f$ 0.37; 1:10:90 ammonia(880)/methanol/dichloromethane) of the two steps was obtained as a white solid: $^1$H NMR (300 Hz, $d_6$-DMSO) 7.46(1H, d), 7.43(2H, dd), 7.37(2H, d), 7.04(1H, t), 6.67(1H, s), 4.31(2H, s), 2.85(2H, dd), 2.45(2H, t), 1.53(2H, m), 1.37(2H, m), 1.21 (12H, m).

EXAMPLE 35

N-[2-(4(5)-Imidazoyl)ethyl]-N'-phenylmethylsulfamide 4-(2-Aminoethyl)-1-(triphenylmethyl)-imidazole (Example 17 step b) was converted to N-2-[1-(triphenylmethyl)imidazol-4-yl]ethyl-N'-tertbutoxycarbonyl-sulfamide according to the procedure of Example 12 step a. The subsequent alkylation with benzyl bromide was performed essentially as Example 12 step b and gave N-[2-(1-(triphenylmethyl)imidazol-4-yl)ethyl]-N'-tert-butoxycarbonyl-N'-phenylmethyl-sulfamide. The final deprotection was carried out in the manner of Example 17 step b and the title compound ($R_f$ 0.21; 1:10:90 ammonia (880)/methanol/dichloromethane) was isolated as a colourless oil: $^1$H NMR (300 Hz, $d_6$-DMSO) 7.50(1H, s), 7.30(6H, m), 6.95(1H, t), 6.78(1H, s), 3.96(2H, s), 3.03(2H, dd), 2.65(2H, t). The maleate salt was prepared by lyophilysis of an equimolar solution of the product and maleic acid in water/dioxan. Found: C 48.05, H 5.10, N 13.87%; $C_{16}H_2ON_4O_6S$ requires: C 48.48, H 5.09 N 14.13%.

EXAMPLE 36

N-[3-(4(5)-Imidazoyl)propyl]-N'-phenylmethyl-sulfamide

The title compound was prepared according to the procedure for Example 35, using 4-(3-aminopropyl)-1-(triphenylmethyl)-imidazole (Example 14 step b) as the initial substrate, and was isolated as a white solid ($R_f$ 0.10; 1:10:90 ammonia(880)/methanol/dichloromethane): $^1$H NMR (300 Hz, $d_6$-DMSO) 11.75(1H, br s), 7.49(1H, s), 7.30(5H, m), 7.25(1H, m), 6.96(1H, t), 6.71(1H, s), 3.98(2H, s), 2.82(2H, m), 2.48(2H, m), 1.72(2H, m). Found: C 53.03, H 6.19, N 18.89%; $C_{13}H_{18}N_4O_2S$ requires: C 53.04, H 6.16, N 19.03%.

EXAMPLE 37

N-[2-(4(5)-Imidazoyl)ethyl]-N'-(4-chlorophenyl)methyl-sulfamide

The title compound was prepared according to the procedure for Example 35, using 4-chlorobenzyl bromide in the alkylation step, and was isolated as a white solid ($R_f$ 0.20; 1:10:90 ammonia(880)/methanol/dichloromethane): $^1$H NMR (300 Hz, $d_6$-DMSO) 11.75(1H, br s), 7.51(1H, s), 7.36(5H, m), 6.99(1H, t), 6.75(1H, s), 3.96(2H, s), 3.01(2H, dd), 2.65(2H, t). Found: C 45.47, H 4.83, N 17.93%; $C_{12}H_{15}ClN_4O_2S$ requires: C 45.79 H 4.80, N 17.80%.

EXAMPLE 38

N-[7-(4(5)-Imidazoyl)heptyl]-N'-(4-chlorophenyl)methyl-sulfamide

The title compound was prepared according to the procedure for Example 12, using 5-(7-aminoheptyl)-1-(N,N-dimethylsulfamoyl)-imidazole (Example 29 step d) as the substrate in step a. The product ($R_f$ 0.28; 1:10:90 ammonia (880)/methanol/dichloromethane) of the three steps was obtained as a white solid: $^1$H NMR (300 Hz, $d_6$-DMSO) 7.45(1H, s), 7.36(5H, m), 6.84(1H, t), 6.67(1H, s), 3.98(2H, s), 2.79(2H, dd), 2.46(2H, t), 1.53(2H, m), 1.37(2H, m), 1.23(6H, m). Found C 53.17, H 6.62, N 14.53%. $Cl_7H2ClN_4O_2S$ requires C 53.05, H 6.55, N 14.56%

EXAMPLE 39

N-[8-(4(5)-Imidazoyl)octyl]-N'-(4-chlorophenyl)methyl-sulfamide

The title compound was prepared according to the procedure for Example 12, using 5-(8-aminooctyl)-1-(N,N-dimethylsulfamoyl)-imidazole as the substrate in step a. The product ($R_f$ 0.30; 1:10:90 ammonia(880)/methanol/ dichloromethane) of the three steps was obtained as a white solid: $^1$H NMR (300 Hz, $d_6$-DMSO) 7.45(1H, s), 7.36(5H, m), 6.82(1H, t), 6.67(1H, s), 3.98(2H, d), 2.74(2H, dd), 2.45(2H, t), 1.55(2H, m), 1.37(2H, m), 1.23(8H, m).

EXAMPLE 40

N-[10-(4(5)-Imidazoyl)decyl]-N'-(4-chlorophenyl)methyl-sulfamide 5-(10-Aminodecyl)-2-(tert-butyldimethylsilyl)-1-(N,N-dimethylsulfamoyl)-imidazole was prepared according to the procedure of Example 33 steps a, b and c, using 1,10-dibromodecane as the alkylating reagent in step a. This amine was converted to the title compound according to the procedure of Example 12. The product ($R_f$ 0.41; 1:10:90 ammonia(880)/methanol/dichloromethane) was isolated as a white solid: $^1$H NMR (300 Hz, $d_6$-DMSO) 7.45(1H, s), 7.35(5H, m), 6.82(1H, t), 6.66(1H, s), 3.98(2H, d), 2.74(2H, dd), 2.45(2H, t), 1.53(2H, m), 1.37(2H, m), 1.21(12H, m). Found C 55.97, H 7.55, N 12.88%. $C_{20}H_{31}ClN_4O_2S$ requires C 56.26, H 7.32, N 13.12%

EXAMPLE 41

N-[4-(4(5)-Imidazoyl)butyl]-N'-(3,4-dichlorophenyl)methyl-sulfamide

The title compound was prepared according to the procedure for Example 12, using 5-(4-aminobutyl)-1-(N,N-dimethylsulfamoyl)-imidazole as the substrate in step a and 3,4-dichlorobenzyl bromide in step b. The product ($R_f$ 0.26; 1:10:90 ammonia(880)/methanol/dichloromethane) was obtained as a white solid: 1H NMR (300 Hz, $CDCl_3$) 7.51(1H, d), 7.42(2H, m), 7.19(1H, dd), 6.76(1H, d), 4.17 (2H, s), 3.06(2H, t), 2.62(2H, t), 1.68(2H, quint.), 1.59(2H, quint.). The maleate salt was prepared by lyophilysis of an equimolar solution of the product and maleic acid in water/dioxan.

EXAMPLE 42

N-[4-(4(5)-Imidazoyl)butyl]-N'-(3-chlorophenyl)methyl-sulfamide

The title compound was prepared according to the procedure for Example 12, using 5-(4-aminobutyl)-1-(N,N-dimethylsulfamoyl)-imidazole[1] as the substrate in step a and 3-chlorobenzyl bromide in step b. The product ($R_f$ 0.26; 1:10:90 ammonia(880)/methanol/dichloromethane) was obtained as a white solid: $^1$H NMR (300 Hz, $d_6$-DMSO) 11.73(1H, br s), 7.47(1H, d), 7.35(5H, m), 6.88(1H, t), 6.69(1H, s), 4.00(2H, d), 2.79(2H, dd), 2.45(2H, t), 1.55(2H, m), 1.42(2H, m). The maleate salt was prepared by lyophilysis of an equimolar solution of the product and maleic acid in water/dioxan.

EXAMPLE 43

N-[4-(4(5)-Imidazoyl)butyl]-N'-(2-chlorophenyl)methyl-sulfamide

The title compound was prepared according to the procedure for Example 12, using 5-(4-aminobutyl)-1-(N,N-dimethylsulfamoyl)-imidazole as the substrate in step a and 2-chlorobenzyl bromide in step b. The product ($R_f$ 0.26; 1:10:90 ammonia(880)/methanol/dichloromethane) was obtained as a white solid: $^1$H NMR (300 Hz, $d_6$-DMSO) 1.75(1H, br s), 7.53(1H, d), 7.47(1H, s), 7.35(4H, m), 6.95(1H, t), 6.68(1H, s), 4.09(2H, d), 2.83(2H, dd), 2.45(2H, t), 1.55(2H, m), 1.46(2H, m). The maleate salt was prepared by lyophilysis of an equimolar solution of the product and maleic acid in water/dioxan.

EXAMPLE 44

N-[4-(4(5)-Imidazoyl)butyl]-N'-(4-iodophenyl) methyl-sulfamide

The title compound was prepared according to the procedure for Example 12, using 5-(4-aminobutyl)-1-(N,N-dimethylsulfamoyl)-imidazole[1] as the substrate in step a and 4-iodobenzyl bromide in step b. The product ($R_f$ 0.24; 1:10:90 ammonia(880)/methanol/dichloromethane) was obtained as a white solid: $^1$H NMR (300 Hz, $d_6$-DMSO) 11.75(1H, br s), 7.67(2H, d), 7.49(1H, s), 7.33(1H, t), 7.14(2H, d), 6.85(1H, t), 6.70(1H, s), 3.94(2H, d), 2.79(2H, dd), 2.46(2H, t), 1.55(2H, m), 1.46(2H, m). The maleate salt was prepared by lyophilysis of an equimolar solution of the product and maleic acid in water/dioxan.

EXAMPLE 45

N-[4-(4(5)-Imidazoyl)butyl]-N'-(4-bromophenyl) methyl-sulfamide

Step a

N-[4-(1-(N'',N''-Dimethylsulfamoyl)imidazol-4-yl) butyl]-N'-tert-butoxycarbonyl-sulfamide 5-(4-Aminobutyl)-1-(N,N-dimethylsulfamoyl)-imidazole[1] was converted to the product according to the procedure of Example 12 step a.

Step b

N-[4-(1-(N'',N''-Dimethylsulfamoyl)imidazol-4-yl) butyl]-N'-(4 -bromophenyl)methyl-N'-tert-butoxycarbonyl-sulfamide (A)

The product from step a (500 mg, 1.27 mmol) was allowed to react with 4-bromobenzyl bromide in the manner of Example 12 step b. The crude product mixture was purified by flash column chromatography (silica; 50% ethyl acetate/dichloromethane) and gave the product (A) ($R_f$ 0.37) as a yellow oil (267 mg, 35%) and N,N'-di-[(4-bromophenyl)methyl]-N-[(1-(N'',N''-dimethylsulfamoyl) imidazol-4-yl)butyl]-N'-tert-butoxycarbonyl-sulfamide (B) ($R_f$ 0.56) (220 mg, 23%).

Step c

The product (A) from step b was deprotected according to the procedure of Example 12 step c and the title compound ($R_f$ 0.28; 1:10:90 ammonia(880)/methanol/dichloromethane) was obtained as a white solid: $^1$H NMR (300 Hz, $d_6$-DMSO) 7.50(3H, m), 7.35(1H, t), 7.28(2H, d), 6.87(1H, t), 6.71(1H, s), 3.96(2H, d), 2.78(2H, dd), 2.46(2H, t), 1.55(2H, m), 1.42(2H, m). The maleate salt was prepared by lyophilysis of an equimolar solution of the product and maleic acid in water/dioxan. Found: C 40.66, H 4.90, N 10.67%; $C_{18}H23BrN_4O_6S.1.5H_2O$ requires: C 40.76, H 4.94, N 10.56%.

EXAMPLE 46

N-[4-(4(5)-Imidazoyl)butyl]-N'-(4-fluorophenyl) methyl-sulfamide

The title compound was prepared according to the procedure for Example 12, using 5-(4-aminobutyl)-1-(N,N-dimethylsulfamoyl)-imidazole[1] as the substrate in step a and 4-fluorobenzyl bromide in step b. The product ($R_f$ 0.26; 1:10:90 ammonia(880)/methanol/dichloromethane) was obtained as a white solid: $^1$H NMR (300 Hz, $d_6$-DMSO) 11.67(1H, br s), 7.46(1H, s), 7.35(3H, m), 7.14(2H, m), 6.85(1H, t), 6.68(1H, s), 3.97(2H, d), 2.79(2H, dd), 2.46(2H, m), 1.54(2H, m), 1.45(2H, m). The maleate salt was prepared by lyophilysis of an equimolar solution of the product and maleic acid in water/dioxan. Found: C 44.92, H 5.61, N 11.42%; $C_{18}H_{23}FN_4O_6S.2.0H_2O$ requires: C 45.18, H 5.69, N 11.71%.

EXAMPLE 47

N-[4-(4(5)-Imidazoyl)butyl]-N'-(4-(trifluoromethyl) phenyl)methyl-sulfamide The title compound was prepared according to the procedure for Example 12, using 5-(4-aminobutyl)-1-(N,N-dimethylsulfamoyl)-imidazole[1] as the substrate in step a and 4-(trifluoromethyl)benzyl bromide in step b. The product ($R_f$ 0.26; 1:10:90 ammonia(880)/methanol/dichloromethane) of the three steps was obtained as a white solid: $^1$H NMR (300 Hz, $d_6$-DMSO) 11.70(1H, br s), 7.68(2H, d), 7.54(2H, d), 7.44(2H, m), 6.90(1H, t), 6.68(1H, s), 4.09(2H, d), 2.80(2H, dd), 2.45(2H, t), 1.55(2H, m), 1.45(2H, m). The maleate salt was prepared by lyophilysis of an equimolar solution of the product and maleic acid in water/dioxan. Found: C 43.17, H 4.99, N 10.88%; $C_{19}H_{23}F_3N_4O_6S.2.0H_2O$ requires: C 43.18, H 5.15, N 10.60%.

EXAMPLE 48

N-[4-(4(5)-Imidazoyl)butyl]-N'-(4-methoxyphenyl) methyl-sulfamide

The title compound was prepared according to the procedure for Example 12, using 5-(4-aminobutyl)-1-(N,N-dimethylsulfamoyl)-imidazole[1] as the substrate in step a and 4-methoxybenzyl bromide in step b. The product ($R_f$ 0.26; 1:10:90 ammonia(880)/methanol/dichloromethane) was obtained as a white solid: $^1$H NMR (300 Hz, $d_6$-DMSO) 11.70(1H, br s), 7.47(1H, s), 7.22(2H, d), 7.18(1H, t), 6.87(2H, d), 6.79(1H, t), 6.68(1H, s), 3.90(2H, d), 3.72(3H, s), 2.79(2H, dd), 2.45(2H, t), 1.55(2H, m), 1.44(2H, m). The maleate salt was prepared by lyophilysis of an equimolar solution of the product and maleic acid in water/dioxan. Found: C 50.19, H 5.80, N 12.36%; $Cl_9H_{26}N_4O_7S$ requires: C 50.21, H 5.77, N 12.33%.

EXAMPLE 49

N-[4-(4(5)-Imidazoyl)butyl]-N'-(4-biphenyl)methyl-sulfamide 5-(4-Aminobutyl)-2-(tert-butyldimethylsilyl)-1-(N,N-dimethylsulfamoyl)-imidazole was isolated as a by-product during the preparation of 5-(4-aminobutyl)-1-(N,N-dimethylsulfamoyl)-imidazole,[1] in analogous fashion to Example 33. It was converted to the title compound using the procedure for Example 12, using (4-chloromethyl) biphenyl as the substrate in step b. Step b was further modified by heating the reaction mixture at 50° C. for 2 h prior to work up. The product ($R_f$ 0.28; 1:10:90 ammonia (880)/methanol/dichloromethane) was obtained as a white solid: $^1$H NMR (300 Hz, $d_6$-DMSO) 11.75(1H, br s), 7.63 (4H, m), 7.42(5H, m), 7.33(2H, m), 6.86(1H, t), 6.69(1H, s), 4.03(2H, d), 2.82(2H, dd), 2.46(2H, t), 1.54(2H, m), 1.45 (2H, m). The maleate salt was prepared by lyophilysis of an equimolar solution of the product and maleic acid in water/dioxan. Found: C 54.71, H 5.87, N 10.80%; $C_{24}H_{28}N_4O_6S.1.5H_2O$ requires: C 54.63, H 5.92, N 10.61%.

EXAMPLE 50

N-[4-(4(5)-Imidazoyl)butyl]-N'-2-naphthylmethyl-sulfamide

The title compound was prepared according to the procedure for Example 12, using 5-(4-aminobutyl)-2-(tert-butyldimethylsilyl)-1-(N,N-dimethylsulfamoyl)-imidazole (Example 49) as the substrate in step a and 2-bromomethyl-naphthalene in step b. The product ($R_f$ 0.24; 1:10:90 ammonia(880)/methanol/dichloromethane) was obtained as a white solid: $^1$H NMR (300 Hz, $d_6$-DMSO) 11.70(1H, br s), 7.85(4H, m), 7.48(4H, m), 7.40(1H, t), 6.88(1H, t), 6.71 and 6.58 (1H, 2×br s), 4.16(2H, d), 2.83(2H, dd), 2.43(2H, m), 1.53(2H, m), 1.45(2H, m). The maleate salt was prepared by lyophilysis of an equimolar solution of the product and maleic acid in water/dioxan. Found: C 55.49, H 5.66, N 11.59%; $C_{22}H_{26}N_4O_6S$ requires: C 55.68, H 5.52, N 11.81%.

EXAMPLE 51

N-[4-(4(5)-Imidazoyl)butyl]-N'-cyclohexylmethyl-sulfamide

Step a

(Z)-4-[4-(1,3-Dioxolan-2-yl)but-2-ethyl]-1-(triphenylmethyl)-imidazole

A suspension of [2-(1,3-dioxolan-2-yl)ethyl]triphenylphosphonium bromide (48.54 g, 109 mmol) in dry tetrahydrofuran (500 ml) was cooled, under an atmosphere of argon, to −20° C. n-Butyl lithium (1.6M in hexanes) (68.3 ml, 109 mmol) was added dropwise and the solution stirred for a 1 h. A solution of [1-(triphenylmethyl)imidazol-4-yl]carbaldehyde[4] (36.80 g, 109 mmol) in dry tetrahydrofuran (500 ml) was added slowly dropwise and the reaction mixture stirred at room temperture for 18 h. The reaction mixture was concentrated in vacuo, water was added and the mixture filtered through pad of Celite. The filtrate was extracted with dichloromethane (2×500 ml) and the combined extracts dried over magnesium sulfate. Filtration and evaporation gave a yellow oil. From flash column chromatography (silica; 10–20% ethyl acetate/hexane) the product was isolated as a yellow oil (19.73 g, 42%).

Step b

4-[4-(1,3-Dioxolan-2-yl)butyl]-1-(triphenylmethyl)-imidazole

A solution of the product from step a in ethanol was hydrogenated in the presence of a catalytic quantity of 10% palladium-on-charcoal at atmospheric pressure and temperature for 18 h. The product was isolated as a colourless oil in quantitative yield.

Step c

4-[1-(Triphenylmethyl)imidazol-4-yl]butan-1-al

A suspension of the product from step b (19.8 g, 46.6 mmol) in a mixture of acetone (300 ml) and 2M hydrochloric acid (50 ml) was stirred at room temperature for 20 h. The mixture was neutralised with sodium hydrogen carbonate, filtered and the filtrate extracted with dichloromethane (3×100 ml). The combined extracts were dried over magnesium sulfate, filtered and evaporated to give the product as a colourless oil (16.1 g, 91%).

Step d

4-[1-(Triphenylmethyl)imidazol-4-yl]butan-1-ol

A solution of the product from step c (16.1 g, 42.4 mmol) in ethanol (300 ml) was cooled under an atmosphere of argon to 0° C. Sodium borohydride (1.57 g, 42.4 mmol) was added, the mixture stirred for 4 h and carefully quenched with saturated ammonium chloride. The mixture was extracted with dichloromethane (3×100 ml). The combined extracts were dried over magnesium sulfate, filtered and evaporated to give a white solid, which was dissolved in a 5% methanol/dichloromethane and preciptated with diethyl ether. Thus, the product was isolated as a colourless crystalline solid (9.34 g, 58%).

Step e

N-tert-Butoxycarbonyl-N'-cyclohexylmethyl-sulfamide

Cyclohexylmethylamine was converted to the product using essentially the procedure described in step a of Example 12.

Step f

N-tert-Butoxycarbonyl-N-[4-[1-(triphenylmethyl)imidazol-4-yl]butyl]-N'cyclohexylmethyl-sulfamide To a solution of the product from step d (764 mg, 2.00 mmol), the product from step e (642 mg, 2.20 mmol) and triphenylphosphine 576 mg, 2.20 mmol) in dry tetrahydrofuran (20 ml), under an atmosphere of argon, was added over 10 min a solution of diethylazodicarboxylate (383 mg, 2.20 mmol) in dry tetrahydrofuran (5 ml). The mixture was stirred for 2 h, the solvent evaporated and the residue purified by flash column chromatography (silica; 30% ethyl acetate/dichloromethane). Thus, the product was isolated as a colourless foam (800 mg, 60%).

Step g

A solution of the product of step f (800 mg, 1.20 mmol) in a mixture of ethanol (15 ml) and 2M hydrochloric acid (5 ml) was heated at reflux for 2 h. The solvent was evaporated and the residue purified by flash column chromatography (silica; 1:10:90 ammonia(880)/methanol/dichloromethane). Thus, the title compound ($R_f$ 0.28) was isolated as a white solid (184 mg, 49%). The maleate salt was prepared by lyophilysis of an equimolar solution of the product and maleic acid in water/dioxan: $^1$H NMR (300 Hz, $d_6$-DMSO) 8.87(1H, s), 7.36(1H, s), 6.70(1H, t), 6.02(1H, s), 2.80(2H, dd), 2.61(4H, m), 1.63(7H, m), 1.44(3H, m), 1.13(3H, m), 0.83(2H, m).

EXAMPLE 52

N-[4-(4(5)-Imidazoyl)butyl]-N'-adamant-1-ylmethyl-sulfamide

The title compound was prepared according to the procedure for Example 51, using 1-adamant-1-ylmethylamine as the substrate in step e. The product ($R_f$ 0.32; 1:10:90 ammonia(880)/methanol/dichloromethane) was obtained as a white solid: 1H NMR (300 Hz, $d_6$-DMSO) 11.66(1H, br s), 7.45(1H, s), 6.70(1H, br s), 6.66(1H, t), 6.57(1H, t), 2.78 (2H, m), 2.48(4H, m), 1.91(3H, s), 1.56(8H, m), 1.44(8H, m). The maleate salt was prepared by lyophilysis of an equimolar solution of the product and maleic acid in water/dioxan.

EXAMPLE 53

N-[3-(4(5)-Imidazoyl)propyl]-2-(4-chlorophenyl)ethanesulfonamide

Step a

N-[3-(1-(triphenylmethyl)imidazoyl-4-yl)propyl]-2-(4-chlorophenyl)ethanesulfonamide 4-(3-Aminopropyl)-1-(triphenylmethyl)-imidazole (Example 14 step b) (500 mg, 1.01 mmol) and 2-(4- chlorophenyl)ethanesulfonyl chloride (prepared essentially as Example 4 step a) (266 mg, 1.01 mmol) were reacted together in the presence of triethylamine (155 μl, 1.94 mmol) according to the procedure of Example 9 step a. The product was isolated as a colourless foam (494 mg, 86%).
Step b The product from step a (494 mg, 0.87 mmol) was deprotected according to the procedure of Example 17 step d and the title compound was isolated as a white solid (154 mg, 54%): $^1$H NMR (300 Hz, d$_4$-MeOH) 7.66(1H, s), 7.38(2H, d), 7.63(2H, d), 6.90(1H, s), 3.37(2H, m), 3.14(4H, m), 2.74(2H, t), 1.94(2H, quint.). Found C 51.25, H 5.61, N 12.72%. $C_{14}H_{18}ClN_3O_2S$ requires C 51.29, H 5.53, N 12.82%.

EXAMPLE 54

N-[5-(4(5)-Imidazoyl)pentyl]-2-(4-chlorophenyl)ethanesulfonamide

Step a

N-[5-(2-(tert-Butyldimethylsilyl)-1-(N',N'-dimethylsulfamoyl)imidazol-4-yl)pentyl]-2-(4-chlorophenyl)ethanesulfonamide 5-(5-Aminopentyl)-2-(tert-butyldimethylsilyl)-1-(N,N-dimethylsulfamoyl)-imidazole was isolated as a by-product during the preparation of 5-(5-aminopentyl)-1-(N,N-dimethylsulfamoyl)-imidazole,[1] in analogous fashion to Example 33. It was allowed to react with 2-(4-chlorophenyl)ethanesulfonyl chloride (prepared essentially as Example 4 step a) in the manner of Example 9 step a. The product was obtained as a yellow oil.

Step b

The product from step a (494 mg, 0.87 mmol) was deprotected according to the procedure of Example 12 step c and the title compound was isolated as a white solid (227 mg, 92%): $^1$H NMR (300 Hz, d$_4$-MeOH) 7.58(1H, s), 7.34(2H, d), 7.29(2H, d), 6.80(1H, s), 3.31(2H, m), 3.09(4H, m), 2.63(2H, m), 1.70(2H, m), 1.60(2H, m), 1.44(2H, m). Found C 54.04, H 6.27, N 11.55%. $C_{16}H_{22}ClN_3O_2S$ requires C 54.00, H 6.23, N 11.83%.

EXAMPLE 55

N-[4-(4(5)-Imidazoyl)butyl-2-(4-chlorophenyl)ethanesulfonamide

The title compound was prepared according to the procedure for Example 54, using 5-(4-aminobutyl)-1-(N,N-dimethylsulfamoyl)-imidazole[1] as the amine component in step a. The product was obtained as a white solid: $^1$H NMR (300 Hz, CDCl$_3$) 7.56(1H, s), 7.30(2H, dd), 7.16(2H, d), 6.78(1H, s), 4.55 (1 h br s), 3.25(2H, m), 3.09(4H, m), 2.64(2H, t), 1.72(2H, quint.), 1.58(2H, quint.). Found C 52.52, H 5.92, N 12.11%. $Cl_5H_{20}ClN_3O_2S$ requires C 51.70, H 5.90, N 12.29%

EXAMPLE 56

N-[3-(4(5)-Imidazoyl)propyl]-N'-2-(4-chlorophenyl)ethyl-sulfamide

Step a

N-tert-Butoxycarbonyl-N'-2-(4chlorophenyl)ethyl-sulfamide 2-(4-chlorophenyl)ethylamine was converted to the product using essentially the procedure described in step a of Example 12.

Step b

N-tert-Butoxycarbonyl-N-[3-[1-(triphenylmethyl)imidazol-4-yl]propyl]-N'-2-(4-chlorophenyl)ethyl-sulfamide The product from step a and 3-[1-(triphenylmethyl)imidazol-4-yl]propan-1-ol[3] were allowed to react together under the conditions of Example 51 step f. The product was isolated as a white foam.

Step c

The product from step b was deprotected according to the procedure of Example 12 step c and the title compound was isolated as a white solid: $^1$H NMR 25 (300 Hz, d$_4$-MeOH) 7.58(1H, s), 7.28(4H, m), 6.82(1H, s), 3.20(2H, t), 2.86(4H, m), 2.64(2H, t), 1.83(2H, quint.). The maleate salt was prepared by lyophylisis of an equimolar solution of the product and maleic acid in water/dioxan. Found C 46.87, H 5.14, N 12.36%. $C_{18}H_{23}ClN_4O_6S$ requires C 47.11, H 5.05, N 12.21%.

EXAMPLE 57

N-[4-(4(5)-Imidazoyl)butyl]-N'-2-(4-chlorophenyl)ethyl-sulfamide

The title compound was prepared according to the procedure for Example 56, using 4-[1-(triphenylmethyl)imidazol-4-yl]butan-1-ol (Example 51 step d) in step b. The product was obtained as colourless oil: $^1$H NMR (300 Hz, d4-MeOH) 7.53(1H, s), 7.24(4H, m), 6.75(1H, s), 3.15(2H, t), 2.83(4H, m), 2.57(2H, t), 1.57(4H, m). The maleate salt was prepared by lyophylisis of an equimolar solution of the product and maleic acid in water/dioxan. Found C 48.28, H 5.44, N 11.62%. $Cl_9H_{25}ClN_4O_6S$ requires C 48.25, H 5.33, N 11.85%

EXAMPLE 58

N-[6-(4(5)-Imidazoyl])hexyl]-N'-(4-bromophenyl)methyl-sulfamide

The title compound was prepared according to the procedure for Example 12, using 5-(6-aminohexyl)-1-(N,N-dimethylsulfamoyl)-imidazole[1] as the substrate in step a and 4-bromobenzyl bromide in step b. The product was obtained as a white solid: $^1$H NMR (300 Hz, d$_6$-DMSO) 7.52(3H, m), 7.37(1H, t), 7.31(2H, d), 6.86(1H, t), 6.70(1H, s), 3.99(2H, d), 2.77(2H, dd), 2.48(2H, t), 1.55(2H, m), 1.41(2H, m), 1.28(4H, m). The maleate salt was prepared by lyophylisis of an equimolar solution of the product and maleic acid in water/dioxan. Found C 44.92, H 5.17, N 10.58%. $C_{20}H_{27}BrN_4O_6S$ requires C 45.20, H 5.12, N 10.54%

EXAMPLE 59

N-[6-(4(5)-Imidazoyl)hexyl]-N'-(4-fluorophenyl)methyl-sulfamide

The title compound was prepared according to the procedure for Example 12, using 5-(6-aminohexyl)-1-(N,N-dimethylsulfamoyl)-imidazole[1] as the substrate in step a and 4-fluorobenzyl bromide in step b. The product was obtained as a white solid: $^1$H NMR (300 Hz, d$_6$-DMSO) 11.50(1H, br s), 7.48(1H, s), 7.35(3H, m), 7.16(2H, m), 6.86(1H, t), 6.70(1H, s), 4.00(2H, d), 2.78(2H, dd), 2.48(2H, t), 1.55(2H, m), 1.42(2H, m), 1.28(4H, m). The maleate salt was prepared by lyophylisis of an equimolar solution of the product and maleic acid in water/dioxan. Found C 51.25, H 5.79, N 11.72%. $C_{20}H_{27}FN_4O_6S$ requires C 51.05, H 5.78, N 11.91%.

EXAMPLE 60

N-[6-(4(5)-Imidazoyl)hexyl]-N'-(4-(trifluoromethyl)phenyl)methyl-sulfamide

The title compound was prepared according to the procedure for Example 12, using 5-(6-aminohexyl)-1-(N,N-dimethylsulfamoyl)-imidazole[1] as the substrate in step a and 4-(trifluoromethyl)benzyl bromide in step b. The product was obtained as a white solid: $^1$H NMR (300 Hz, d$_6$-DMSO) 11.70(1H, br s), 7.70(2H, d), 7.58(2H, d), 7.49(1H, s), 7.47(1H, s), 6.91(1H, t), 6.70(1H, s), 4.12(2H, d), 2.78(2H, dd), 2.48(2H, t), 1.54(2H, m), 1.41(2H, m), 1.27(4H, m). The maleate salt was prepared by lyophilysis of an equimolar solution of the product and maleic acid in water/dioxan.

EXAMPLE 61

N-[6-(4(5)-Imidazoyl)hexyl]-N'-(4-iodophenyl)methyl-sulfamide

The title compound was prepared according to the procedure for Example 12, using 5-(6-aminohexyl)-1-(N,N-dimethylsulfamoyl)-imidazole[1] as the substrate in step a and 4-iodobenzyl bromide in step b. The product was obtained as a white solid: $^1$H NMR (300 Hz, d$_6$-DMSO) 11.75(1H, br s), 7.67(2H, d), 7.45(1H, s), 7.33(1H, t), 7.14(2H, d), 6.82(1H, t), 6.67(1H, s), 3.94(2H, d), 2.74(2H, dd), 2.46(2H, t), 1.52(2H, m), 1.37(2H, m), 1.25(4H, m). The maleate salt was prepared by lyophilysis of an equimolar solution of the product and maleic acid in water/dioxan. Found C 41.62, H 4.75, N 9.59%. $C_{20}H_{21}N_4O_6S$ requires C 41.53, H 4.71, N 9.69%.

EXAMPLE 62

N-[6-(4(5)-Imidazoyl)hexyl]-N'-(4biphenyl)methyl-sulfamide

The title compound was prepared according to the procedure for Example 49, using 5-(6-aminohexyl)-1-(N,N-dimethylsulfamoyl)-imidazole.[1] The product was obtained as a white solid: 1H NMR (300 Hz, d$_6$-DMSO): 11.75(1H, br s), 7.62(4H, m), 7.42(5H, m), 7.33(2H, m), 6.83(1H, t), 6.66(1H, s), 4.03(2H, d), 2.78(2H, dd), 2.44(2H, t), 1.51(2H, m), 1.38(2H, m), 1.26(4H, m). The maleate salt was prepared by lyophilysis of an equimolar solution of the product and maleic acid in water/dioxan.

EXAMPLE 63

N-[5-(4(5)-Imidazoyl)pentyl]-N'-(4-(trifluoromethyl)phenyl)methyl-sulfamide

The title compound was prepared according to the procedure for Example 12, using 5-(5-aminopentyl)-2-(tert-butyldimethylsilyl)-1-(N,N-dimethylsulfamoyl)-imidazole (Example 54 step a) as the substrate in step a and 4-(trifluoromethyl)benzyl bromide in step b. The product was obtained as a white crystalline solid: $^1$H NMR (300 Hz, d$_4$-MeOH) 7.62(2H, d), 7.56(3H, m), 6.75(1H, s); 4.40(2H, s), 2.92(2H, t), 2.57(2H, t), 1.63(2H, quint.), 1.55(2H, quint.), 1.38(2H, m).

EXAMPLE 64

N-[5-(4(5)-Imidazoyl)pentyl]-N'-(4-bromophenyl)methyl-sulfamide

The title compound was prepared according to the procedure for Example 12, using 5-(5-aminopentyl)-2-(tert-butyldimethylsilyl)-1-(N,N-dimethylsulfamoyl)-imidazole (Example 54 step a) as the substrate in step a and 4-bromobenzyl bromide in step b. The product was obtained as a white crystalline solid: $^1$H NMR (300 Hz, d$_4$-MeOH) 7.53(1H, s), 7.47(2H, d), 7.28(2H, d), 6.75(1H, s), 4.08(2H, s), 2.90(2H, t), 2.57(2H, t), 1.63(2H, quint.), 1.50(2H, quint.), 1.38(2H, m).

EXAMPLE 65

N-[5-(4(5)-Imidazoyl)pentyl]-N'-(4-fluorophenyl)methyl-sulfamide

The title compound was prepared according to the procedure for Example 12, using 5-(5-aminopentyl)-1-(N,N-dimethylsulfamoyl)-imidazole[1] as the substrate in step a and 4-fluorobenzyl bromide in step b. The product was obtained as a white solid: $^1$H NMR (300 Hz, d$_4$-MeOH) 7.54(1H, s), 7.37(2H, dd), 7.04(2H, t), 6.75(1H, s), 4.09(2H, s), 2.90(2H, t), 2.50(2H, t), 1.64(2H, quint.), 1.52(2H, quint.), 1.37(2H, m).

EXAMPLE 66

N-[5-(4(5)-Imidazoyl)pentyl]-N'-(4-iodophenyl)methyl-sulfamide

The title compound was prepared according to the procedure for Example 12, using 5-(5-aminopentyl)-1-(N,N-dimethylsulfamoyl)-imidazole[1] as the substrate in step a and 4-iodobenzyl bromide in step b. The product was obtained as a white solid: $^1$H NMR (300 Hz, d$_4$-MeOH) 7.67(2H, d), 7.54(1H, s), 7.16(2H, d), 6.76(1H, s), 4.06(2H, s), 2.89(2H, t), 2.58(2H, t), 1.63(2H, quint.), 1.50(2H, quint.), 1.36(2H, m).

EXAMPLE 67

N,N'-Di-[(4-bromophenyl)methyl]-N-[4-(4(5)-imidazoyl)butyl]-sulfamide

N,N'-Di-[(4-bromophenyl)methyl]-N-[4-(1-(N'',N''-dimethylsulfamoyl)imidazol-4-yl)butyl]-N'-tert-butoxycarbonyl-sulfamide (Example 45, step b, product (B)) was deprotected according to the procedure of Example 12 step c and the title compound (R$_f$ 0.45; 1:10:90 ammonia (880)/methanol/dichloromethane) was obtained as a white solid: $^1$H NMR (300 Hz, CDCl$_3$) 7.43(5H, m), 7.16(4H, d), 6.68(1H, s), 4.27(2H, s), 4.12(2H, s), 3.13(2H, t), 2.53(2H, m), 1.53(4H, m). The maleate salt was prepared by lyophilysis of an equimolar solution of the product and maleic acid in water/dioxan. Found C 44.62, H 4.29, N 8.35%. $C_{25}H_{28}Br_2N_4O_6S$ requires C 44.66, H 4.20, N 8.33%.

EXAMPLE 68

N'-(4-Chlorophenyl)methyl-N,N'-dimethyl-N-[4-(4(5)-imidazoyl)butyl]-sulfamide

Step a

N,N'-Dimethyl-N-[4-(1-(N'',N''-dimethylsulfamoyl)imidazol-4-yl)butyl]-N'-tert-butoxycarbonyl-sulfamide A solution of N-[4-(1-(N'',N''-dimethylsulfamoyl)imidazol-4-yl)butyl]-N'-tert-butoxycarbonyl-sulfamide (Example 45 step a) (686 mg, 1.67 mmol) and iodomethane (218 μl, 3.50 mmol) in dry N,N-dimethylformamide (4 ml) was cooled under an atmosphere of argon to 0° C. Sodium hydride (147 mg, 3.67 mmol) was added and the reaction mixture was stirred and allowed to warm to room temperature overnight. The reaction was quenched with brine and extracted with ethyl acetate (2+50 ml). The combined extracts were washed three times with water, dried over magnesium sulfate, filtered and evaporated to give a yellow oil. Flash column chromatography (silica; 0.5:5:95 ammonia (880)/methanol/dichloromethane) afforded the product as a colourless oil (356 mg, 48%).

Step b

N,N'-Dimethyl-N-[4-(1-(N'',N''-dimethylsulfamoyl) imidazol-4-yl)butyl]-sulfamide A solution of the product from step a (352 mg, 0.80 mmol) in trifluoroacetic acid (1 ml) was stirred for 30 min and the acid evaporated. The residue was dissolved in dichloromethane, neutralised with saturated sodium hydrogen carbonate solution and extracted with dichloromethane (3×10 ml). The combined extracts were dried over magnesium sulfate, filtered and evaporated to give the product in quantitative yield as a colourless oil (271 mg).

Step c

N'-(4-Chlorophenyl)methyl-N,N'-dimethyl-N-[4-(1-(N'',N''-dimethylsulfamoyl)imidazol-4-yl)butyl]-sulfamide The product from step b (315 mg, 0.93 mmol) was alkylated with 4-chlorobenzyl bromide according to the procedure of Example 12 step b. Flash column chromatography (silica; 0.5:5:95 ammonia(880)/methanol/dichloromethane) afforded the product as a pale yellow oil (325 mg, 75%).

Step d

The product from step c (325 mg, 0.70 mmol) was deprotected according to the procedure of Example 12 step c and the title compound was obtained as a white solid (81 mg, 32%): $^1$H NMR (300 Hz, CDCl$_3$) 7.55(1H, d), 7.33(2H, dd), 7.26(2H, dd), 6.78(1H, s), 4.26(2H, s), 3.24(2H, t), 2.81(3H, s), 2.65(5H, m), 1.68(4H, m). The maleate salt was prepared by lyophilysis of an equimolar solution of the product and maleic acid in water/dioxan. Found C 49.04, H 5.73, N 11.39%. $C_{20}H_{27}ClN_4O_6S$ requires C 49.33, H 5.59, N 11.51%

EXAMPLE 69

N'-(4-Chlorophenyl)methyl-N-[4-(4(5)-imidazoyl) butyl]-N-methyl-sulfamide

Step a

N'-(4-Chlorophenyl)methyl-N-[4-(1-(N'',N''-dimethylsulfamoyl)imidazol-4-yl)butyl]-N'-tert-butoxycarbonyl-sulfamide 5-(4-Aminobutyl)-1-(N,N-dimethylsulfamoyl)-imidazole[1] was converted to the product in analogous fashion to Example 12 steps a and b.

Step b

N'-(4-Chlorophenyl)methyl-N-[4-(1-(N'',N''-dimethylsulfamoyl)imidazol-4-yl)butyl]-N-methyl-N'-tert-butoxycarbonyl-sulfamide The product from step a (310 mg, 0.58 mmol) was methylated according to the procedure of Example 68 step a. The product was obtained as a pale yellow oil (309 mg, 97%).

Step c

The product from step b (325 mg, 0.70 mmol) was deprotected according to the procedure of Example 12 step c and the title compound was obtained as a white solid (80 mg, 42%): $^1$H NMR (300 Hz, CDCl$_3$) 7.50(1H, s), 7.32(4H, m), 6.77(1H, s), 4.17(2H, s), 3.18(2H, t), 2.77(3H, s), 2.64(2H, t), 1.66(4H, m). The maleate salt was prepared by lyophilysis of an equimolar solution of the product and maleic acid in water/dioxan. Found C 48.33, H 5.41, N 11.56%. $C_{19}H_{25}ClN_4O_6S$ requires C 48.25, H 5.33, N 11.85%.

EXAMPLE 70

N'-(4-Chlorophenyl)methyl-N-[4-4-(5)-imidazoyl) butyl]-N'-methyl-sulfamide

Step a

N'-(4-Chlorophenyl)methyl-N-[4-(1-(N'',N''-dimethylsulfamoyl)imidazol-4-yl)butyl]-sulfamide The tert-butoxycarbonyl group of N'-(4-chlorophenyl) methyl-N-[4-(1-(N'', N''-dimethylsulfamoyl)imidazol-4-yl) butyl]-N'-tert-butoxycarbonyl-sulfamide (Example 10) (414 mg, 0.77 mmol) was removed according to the procedure of Example 68 step b. The product was obtained as a white solid (290 mg, 86%).

Step b

N'-(4-Chlorophenyl)methyl-N-[4-(1-(N'',N''-dimethylsulfamoyl)imidazol-4-yl)butyl]-N'-methyl-sulfamide The product from step a (290 mg, 0.66 mmol) was methylated according to the procedure of Example 68 step a, using iodomethane (43 μl, 0.69 mmol) and sodium hydride (28 mg, 0.70 mmol). The product was obtained as a colourless oil (49 mg, 17%).

Step c

The product from step b (49 mg, 0.11 mmol) was deprotected according to the procedure of Example 12 step c and the title compound was obtained as a colourless oil (22 mg, 58%): $^1$H NMR (300 Hz, CDCl$_3$) 7.56(1H, s), 7.32(2H, dd), 7.26(2H, dd), 6.76(1H, s), 4.26(2H, s), 3.09(2H, t), 2.68(3H, s), 2.64(2H, t), 1.71(2H, m), 1.61(2H, m). The maleate salt was prepared by lyophilysis of an equimolar solution of the product and maleic acid in water/dioxan. Found C 48.36, H 5.52, N 11.61%. $C_{19}H_{25}ClN_4O_6S$ requires C 48.25, H 5.33, N 11.85%

EXAMPLE 71

(R)-(+)-N-[2-(4(5)-Imidazoyl)-1-methyl-ethyl]-2-naphthalenesulfonamide

The title compound was prepared according to the procedure of Example 3 using (R)-α-methyl-histamine as the amine component. The product ($R_f$ 0.18; 1:10:90 ammonia (880)/methanol/dichloromethane) was obtained as a white foam: $^1$H NMR (300 Hz, CDCl$_3$) 8.42(1H, br s), 7.93(3H, m), 7.80(1H, m), 7.57(2H, m), 7.52(1H, s), 6.72(1H, s), 3.61(1H, m), 2.72(1H, dd), 1.57(1H, dd), 1.11(3H, d); $[\alpha]_D$=+41.8° (c=0.91, 1:9 methanol/dichloromethane). The maleate salt was prepared by lyophilysis of an equimolar solution of the product and maleic acid in water/dioxan. Found: C 55.36, H 5.08, N 9.40%; $C_{20}H_{21}N_3O_6S$ requires: C 55.67, H 4.90, N 9.37%.

EXAMPLE 72

N-[2-(4(5)-Imidazoyl)-trans-cyclopropyl]-2-naphthalenesulfonamide

Step a

2-(1-(Triphenylmethyl)imidazoyl-4-yl)-trans-cyclopropylamine

[2-(1-(Triphenylmethyl)imidazoyl-4-yl)-trans-cyclopropyl]-carbamic acid 1R-(2-naphthyl)ethyl ester was prepared according to Burger's synthesis of the corresponding ethyl ester using R-(+)-2-naphthyl ethanol.[5] It was dissolved in 1:1 methanol/tetrahydrofuran and was hydrogenated in the presence of a catalytic quantity of 10% palladium-on-charcoal at atmospheric pressure and temperature for 18 h. Filtration and evaporation of the reaction mixture afforded the amine product.

Step b

N-[2-(1-(Triphenylmethyl)imidazoyl-4-yl)-trans-cyclopropyl]-2-naphthalenesulfonamide was prepared by the reaction between the product from step a and 2-naphthalenesulfonyl chloride according to the procedure of Example 6 step a.

Step c

The product from step b was deprotected according to the procedure of Example 17 step d and the title compound ($R_f$ 0.26; 1:10:90 ammonia(880)/methanol/dichloromethane) was isolated as a white foam: $^1$H NMR (300 Hz, CDCl$_3$) 8.44(1H, s), 7.92(3H, m), 7.84(1H, dd), 7.62(2H, m), 7.47 (1H, s), 6.72(1H, s), 2.48(1H, m), 2.15(1H, m), 1.27(1H, m), 1.21(1H, m).

EXAMPLE 73

3-(4(5)-Imidazoyl)-2S-(2-naphthalene)sulfonamino-propionic Acid Methyl Ester Step a

3-(1-(Triphenylmethyl)imidazoyl-4-yl)-2S-(2-naphthalene)sulfonamino-propionic Acid Methyl Ester To a solution of triphenylmethylhistidine methyl ester hydrochloride (488 mg, 1.00 mmol) and triethylamine (304 µl, 2.20 mmol) in dry dichloromethane (20 ml), under an atmosphere of argon, was added 2-naphthalenesulfonyl chloride (238 mg, 1.05 mmol). The solution was stirred for 1 h, washed with water (2×20 ml), dried over magnesium sulfate, filtered and evaporated. The residue was recrystallized from 1:2 ethyl acetate/hexane to afford the product as a white solid (438 mg, 73%).

Step b

The product from step a (550 mg, 0.91 mmol) was deprotected according to the procedure of Example 17 step d and the title compound ($R_f$ 0.32; 1:10:90 ammonia(880)/methanol/dichloromethane) was isolated as a white solid (114 mg, 35%): H NMR (300 Hz, d$_6$-DMSO) 11.75(1H, br s), 8.45(1H, d), 8.28(1H, d), 8.09(1H, dd), 8.02(2H, t), 7.68(3H, m), 7.39(1H, d), 6.72(1H, s), 4.08(1H, dd), 3.21 (3H, s), 2.76(2H, m). The maleate salt was prepared by lyophilysis of an equimolar solution of the product and maleic acid in water/dioxan.

EXAMPLE 74

N-[1S-Hydroxymethyl-2-(4(5)-imidazoyl)ethyl]-2-naphthalenesulfonamide

Step a

N-[1S-Hydroxymethyl-2-(1-(triphenylmethyl)imidazoyl-4-yl)ethyl]-2-naphthalenesulfonamide To a solution of the product from Example 73 step a (438 mg, 0.73 mmol) in methanol (6 ml) and tetrahydrofuran (12 ml) was added, with stirring, a mixture of sodium borohydride (378 mg, 10.0 mmol) and lithium chloride (420 mg, 10.0 mmol) in small portions over several hours. The mixture was concentrated in vacuo and partitioned between ethyl acetate and water. The organic layer was washed with brine, dried over magnesium sulfate and evaporated to give the product as a white foam (305 mg, 73%).

Step b

The product from step a (300 mg, 0.52 mmol) was deprotected according to the procedure of Example 17 step d and the title compound ($R_f$ 0.32; 1:10:90 ammonia(880)/methanol/dichloromethane) was isolated as a white solid (56 mg, 33%): $^1$H NMR (300 Hz, d$_6$-DMSO) 8.34(1H, s), 8.09(1H, d), 8.00(2H, m), 7.67(3H, m), 7.41(1H, d), 6.69 (1H, s), 3.25(3H, m), 2.64(1H, dd), 2.46(1H, m). The maleate salt was prepared by lyophilysis of an equimolar solution of the product and maleic acid in water/dioxan.

EXAMPLE 75

3-(4(5)-Imidazoyl)-2S-(2-naphthalene)sulfonamino-propionic acid

Step a

3-(1-(Triphenylmethyl)imidazoyl-4-yl)-2S-(2-naphthalene)sulfonamino-propionic Acid To a solution of triphenylmethylhistidine (398 mg, 1.00 mmol) and triethylamine (304 µl, 2.20 mmol) in dry dichloromethane (20 ml), under an atmosphere of argon, was added 2-naphthalenesulfonyl chloride (238 mg, 1.05 mmol). The solution was stirred for 1 h and water (20 ml) was added. Dilute acetic acid was added until pH5 was reached. The mixure was shaken. The organic layer was washed with brine, dried over magnesium sulfate and evaporated to give the product as a pale yellow solid (486 mg, 83%).

Step b

A solution of the product from step a (486 mg, 0.83 mmol) in trifluoroacetic acid (5 ml) was stirred for 18 h and the solvent evaportated. The residue was triturated with diethyl ether and the resultant white solid recrystallized from propan-2-ol/diethyl ether. The trifluoroacetic acid salt of the title compound ($R_f$ 0.07; 20% methanol/dichloromethane) was isolated as a white solid (115 mg, 30%): $^1$H NMR (300 Hz, d$_6$-DMSO) 8.30(1H, d), 8.00(4H, m), 7.68(3H, m), 6.98(1H, s), 4.06(1H, dd), 2.93(1H, dd), 2.81(2H, dd). Found: C 47.08, H 3.59, N 9.20%; C$_{18}$H$_{16}$F$_3$N$_3$O$_6$S requires: C 47.06, H 3.51, N 9.15%.

EXAMPLE 76

N-[5-(4(5)-Imidazoyl)pentyl]-N'-(2-hydroxyethyl)-sulfamide

Step a

N-[5-(2-(tert-butyldimethylsilyl)-1-(N,"N"-dimethylsulfamoyl)imidazol-4-yl)pentyl]-N'-(2-hydroxyethyl)-sulfamide 5-(5-Aminopentyl)-2-(tert-butyldimethylsilyl)-1-(N,N-dimethylsulfamoyl)-imidazole (Example 54 step a) and 2-bromoethanol were allowed to react with chlorosulfonyl isocyanate according to the procedure of Example 12 step a. A solution of the resultant compound in ethanol was treated with 2M sodium hyroxide (2 equivalents) solution and heated at reflux for 2 min and the solvent was evaporated. Water was added to the residue and the mixture extracted with dichloromethane. The organic layer was dried over magnesium sulfate, filtered and evaporated. The residue was purified by flash column chromatography (silica; 2–4% methanol/dichloromethane) and the product was isolated as a colourless oil.

Step b

The product from step b was deprotected according to the procedure of Example 12 step c. The title compound ($R_f$ 0.35; 1:10:90 ammonia(880)/methanol/dichloromethane) was obtained as a colourless oil: 1H NMR (300 Hz, $d_6$-DMSO) 11.70(1H, brs), 7.46(1H, s), 7.10(1H, t), 6.87 (1H, t), 6.68(1H, s), 3.60(2H, t), 3.12(2H, dd), 2.79(2H, dd), 2.46(2H, t), 1.61(2H, quint.), 1.46(2H, quint.), 1.37(2H, quint.).

EXAMPLE 77

N-[4-(4(5)-Imidazoyl)butyl]-(4-bromophenyl) methanesulfonamide

The title compound was prepared according to the procedure for Example 9, using 5-(4-aminobutyl)-1-(N,N-dimethylsulfamoyl)-imidazole[1] and (4-bromophenyl) methanesulfonyl chloride (prepared essentially as Example 4 step a) as the substrates in step a. The product of the two steps was obtained as a white solid: $^1$H NMR (300 Hz, $d_6$-DMSO) 7.56(1H, s), 7.47(2H, d), 7.30(2H, d), 7.04(1H, t), 6.69(1H, s), 4.28(2H, s), 2.87(2H, dd), 2.46(2H, m), 1.53(2H, quint.), 1.41(2H, quint.). The maleate salt was prepared by lyophilysis of an equimolar solution of the product and maleic acid in water/dioxan.

EXAMPLE 78

N-[4-(4(5)-Imidazoyl)butyl]-(4-trifluoromethylphenyl)methanesulfonamide

The title compound was prepared according to the procedure for Example 9, using 5-(4-aminobutyl)-1-(N,N-dimethylsulfamoyl)-imidazole[1] and (4-trifluoromethylphenyl)methanesulfonyl chloride (prepared essentially as Example 4 step a) as the substrates in step a. The product was obtained as a white solid: $^1$H NMR (300 Hz, $d_4$-MeOH) 7.67(2H, d), 7.60(2H, d), 7.55 (1H, s), 6.76(1H, s), 4.39(2H, s), 3.00(2H, t), 2.57(2H, t), 1.64(2H, quint.), 1.48(2H, quint.). The maleate salt was prepared by lyophilysis of an equimolar solution of the product and maleic acid in water/dioxan.

EXAMPLE 79

N-[4-(4(5)-Imidazoyl)butyl]-(4-fluoromethylphenyl) methanesulfonamide

The title compound was prepared according to the procedure for Example 9, using 5-(4-aminobutyl)-1-(N,N-dimethylsulfamoyl)-imidazole[1] and (4-fluoromethylphenyl) methanesulfonyl chloride (prepared essentially as Example 4 step a) as the substrates in step a. The product was obtained as a white solid: $^1$H NMR (300 Hz, $d_6$-DMSO) 7.47(1H, s), 7.39(2H, dd), 7.18(2H, t), 7.01(1H, t), 6.69(1H, s), 4.28(2H, s), 2.86(2H, dd), 2.48(2H, m), 1.52(2H, quint.), 1.42(2H, quint.). The maleate salt was prepared by lyophilysis of an equimolar solution of the product and maleic acid in water/dioxan.

EXAMPLE 80

N-[4-(4(5)-Imidazoyl)butyl]-N'-(1R-phenylethyl)-sulfamide

The title compound was prepared according to the procedure for Example 51, using (R)-(+)-α-methylbenzylamine as the substrate in step e. The product ($R_f$ 0.24; 1:10:90 ammonia(880)/methanol/dichloromethane) was obtained as a white solid: 1H NMR (300 Hz, $d_6$-DMSO) 11.80(1H, br s), 7.47(1H, s), 7.28(5H, m), 7.21(1H, dd), 6.66(1H, s), 6.65 (1H, t), 4.29(1H, m), 2.65(2H, m), 2.40(2H, t), 1.47(2H, m), 1.41(3H, d), 1.36(2H, m). The maleate salt was prepared by lyophilysis of an equimolar solution of the product and maleic acid in water/dioxan.

EXAMPLE 81

N-[4-(4(5)-Imidazoyl)butyl]-N'-(1S-phenylethyl)-sulfamide

The title compound was prepared according to the procedure for Example 51, using (S)-(+)-α-methylbenzylamine as the substrate in step e. The product ($R_f$ 0.24; 1:10:90 ammonia(880)/methanol/dichloromethane) was obtained as a white solid: $^1$H NMR (300 Hz, $d_6$-DMSO) 11.80(1H, br s), 7.47(1H, s), 7.28(5H, m), 7.21(1H, dd), 6.66(1H, s), 6.65 (1H, t), 4.29(1H, m), 2.65(2H, m), 2.40(2H, t), 1.47(2H, m), 1.41(3H, d), 1.36(2H, m). The maleate salt was prepared by lyophilysis of an equimolar solution of the product and maleic acid in water/dioxan.

EXAMPLE 82

N-[5-(4(5)-Imidazoyl)pentyl]-N'-(4-biphenyl) methyl-sulfamide

The title compound was prepared according to the procedure for Example 49, using 5-(5-aminopentyl)-1-(N,N-dimethylsulfamoyl)-imidazole.[1] The product was obtained as a white solid: $^1$H NMR (300 Hz, $d_4$-MeOH) 7.60(4H, m), 7.52(1H, s), 7.43(4H, m), 7.32(1H, dd), 6.72(1H, s), 4.16 (2H, s), 2.91(2H, t), 2.55(2H, t), 1.59(2H, quint.), 1.51(2H, quint.), 1 .38(2H, quint.).

EXAMPLE 83

N-[5-(4(5)-Imidazoyl)butyl]-N'-(1,1-diphenyl) methyl-sulfamide

The title compound was prepared according to the procedure for Example 51, using $C_1$ C-diphenyl methylamine as the substrate in step e. The product ($R_f$ 0.28; 1:10:90 ammonia(880)/methanol/dichloromethane) was obtained as a white solid: $^1$H NMR (300 Hz, $d_6$-DMSO) 11.70(1H, br s), 8.03(1H, d), 7.46(1H, s), 7.27(1OH, m), 6.76(1H, t), 6.63 (1H, s), 5.42(1H, d), 2.52(2H, t), 2.32(4H, t), 1.36(2H, quint.), 1.19(2H, quint.). The maleate salt was prepared by lyophilysis of an equimolar solution of the product and maleic acid in water/dioxan.

EXAMPLE 84

N-[4-(4(5)-Imidazoyl)butyl]-(4-biphenyl) methanesulfonamide

The title compound was prepared according to the procedure for Example 9, using 5-(4-aminobutyl)-1-(N,N-dimethylsulfamoyl)-imidazole[1] and (4-biphenyl) methanesulfonyl chloride (prepared essentially as Example 4 step a) as the substrates in step a. The product was obtained as a white solid: $^1$H NMR (300 Hz, d$_4$-MeOH) 7.63(4H, m), 7.56(1H, s), 7.48(4H, m), 7.32(1H, m), 6.76(1H, s), 4.34 (2H, s), 3.00(2H, t), 2.58(2H, t), 1.65(2H, quint.), 1.52(2H, quint.). The maleate salt was prepared by lyophilysis of an equimolar solution of the product and maleic acid in water/dioxan.

EXAMPLE 85

N-[4-(4(5)-Imidazoyl)butyl]-N-methyl-2-(4-chlorophenyl)ethanesulfonamide

N-[4-(1-(N',N'-Dimethylsulfamoyl)imidazol-4-yl)butyl]-2-(4-chlorophenyl)ethanesulfonamide, an intermediate in the synthesis of Example 55, was methylated with iodomethane essentially as Example 68 step a. Deprotection according to Example 9 step b gave the title compound as a colourless oil: $^1$H NMR (300 Hz, d$_4$-MeOH) 7.55(1H, d), 7.27(4H, m), 6.78(1H, s), 3.26(2H, m), 3.21(2H, t), 3.06(2H, m), 2.83(3H, s), 2.63(2H, t), 1.64(4H, m). The maleate salt was prepared by lyophilysis of an equimolar solution of the product and maleic acid in water/dioxan.

REFERENCES

1. R. C. Vollinga, W. M. P. B. Mange, R. Leurs, H. Timmerman *J. Med. Chem.* 1995, 38, 266.
2. J. C. Emmett, F. H. Holloway, J. L. Turner *J. C. S. Perkin I* 1979 1341.
3. H. Stark, K. Purand, A. Hüls, X. Ligneau, M. Gaibarg, J.-C. Schwartz, W. Schunack J. Med. Chem. 1996, 39, 1220.
4. J. L. Kelley, C. A. Miller, E. W. McLean *J. Med. Chem.* 1977, 20, 721.
5. A. Burger, M. Bernabe, P. W. Collins *J. Med. Chem.* 1970, 13, 33.H$_3$ receptor bioassay The biological activity of the compounds of the examples was measured using the ileal longitudinal muscle, myenteric plexus assay described by Paton and Aboo Zar (*J. Physiol.* 194, 13–33 (1968)). Male Dunkin-Hartley guinea pigs (250–300 g) were employed. Briefly, a 50 cm portion of ileum proximal to the caecum was removed, after discarding the terminal 20 cm. Ileal segments (3 cm) were cleaned by passing Krebs-Henseleit buffer containing 3 $\mu$M mepyramine gently through the ileum using a Pasteur pipette (size: 13.8 cm length, 0.65 cm diameter). To avoid unnecessary damage to the tissue, Krebs-Henseleit buffer was passed through the ileal segment, while it was lying horizontally on a petri dish. Therefore, the ileum was not over-distended and the buffer flowed through with ease. Each segment was then passed over a Pasteur pipette and the longitudinal muscle layer and adhering myenteric plexus was teased away using moist cotton wool, by stroking tangentially away from the mesenteric attachment. The tissues were suspended in 20 ml organ baths containing Krebs-Henseleit buffer at 37±1° C. and gassed with 95% CO$_2$/5% O$_2$. The tissues were ligated to two parallel stainless steel wires, situated between two platinum electrodes (0.76 cm length, 0.06 cm diameter). All measurements were recorded isometrically (Grass FTO3 transducer). Following an initial loading tension of 1 g, the tissues were stimulated with electrical pulses at a frequency of 0.1 Hz and a pulse duration of 0.5msec, as described by Kosterlitz & Watt (1968). Initially, the tissues were stimulated at supramaximal (1.3 fold times maximal) voltage for a period of 30 min and then the tissues were washed and re-stimulated. A "sighter dose" of the selective histamine H$_3$-receptor agonist, R-($\alpha$)-methylhistamine (0.3 $\mu$M) (Arrang et al., 1987), was administered. Upon generation of response, the "sighter dose" was removed from the tissues by "washout" (6 washes over 60 min) and during this period the electrical stimulation was switched off. The tissues were then re-stimulated and allowed to stabilise prior to the addition of drug treatments, which were allocated on a randomised block basis to the organ baths. Following the incubation period, a single cumulative E/[A] curve was obtained. The experimental E/[A] curve data was expressed as the percentage inhibition of the peak height of electrically-stimulated contraction. Antagonist affinity values were calculated from the degree of rightward shift of the R-($\alpha$)-methylhistamine E/[A] curves using Schild's methods (Arunlatcshama & Schild, 1949).

Histamine H3 Radioligand Binding Assay
Preparation of membranes

Male Dunkin Hartley guinea pigs (200–300 g) were used. The small intestine was rapidly removed (cut ~5 cm from caecum and 5 cm from stomach) and placed in ice-cold 20 mM Hepes-NaOH buffer (pH7.4 at 21±3° C.). The tissue was cut into ~10 cm segments, flushed through with ice-cold 20 mM Hepes-NaOH buffer and placed in a beaker containing fresh buffer at 4° C. 10 cm segments of ileum were threaded onto a glass pipette and the longitudinal muscle myenteric plexus was peeled away from the circular muscle using damp cotton-wool. Longitudinal muscle myenteric plexus was immediately placed in ice-cold Viaspan® solution (~100 ml for tissue from 3 guinea pigs) and placed in the refrigerator for 24 hours.

Pre-soaked tissue was weighed and minced with scissors. The tissue was then homogenised in Viaspan® using a polytron (Kinematica AG; PT-DA 3020/2TS, 3×~1–2 s). 50 ml of 500 mM Tris HCl (pH6.9 at 21±3° C.) was added to the tissue and the mixture centrifuged at 39,800×g for 12 min at 4° C. The supernatant was discarded and rehomogenised in 100 ml ice-cold 20 mM Hepes-NaOH buffer (pH7.4 at 21±3° C.) using a teflon-in-glass homogeniser (setting 10; 3×). The homogenate was recentrifuged at 39,800×g and the pellet resuspended in 20 mM Hepes-NaOH buffer (pH7.4 at 21±3° C.), to a tissue concentration of 50 mg.ml$^{-1}$, using a polytron (Brinkman, PT10, 3×~1 s).
Incubation conditions Guinea pig ileum longitudinal muscle myenteric plexus membranes (400 $\mu$l) were incubated for 165 min at 21±3° C. in a final volume of 500 $\mu$l with 20 mM Hepes-NaOH buffer containing [$^3$H]-R-$\alpha$-methylhistamine (50 $\mu$l; 3 nM) and competing compound. Total and non-specific binding of [$^3$H]-R-$\alpha$-methylhistamine were defined using 50 $\mu$l of buffer and 50 $\mu$l of 10 $\mu$M thioperamide, respectively. The assay was terminated by rapid filtration through Whatman GF/B filters, presoaked (2 hr) in 0. 1% polyethyleneimine, using a Brandell Cell Harvester. The filters were washed (3×3 ml) with ice-cold 50 mM Tris-HCl (pH6.9 at 21±3° C.), transferred into scintillation vials, 5 ml liquid scintillation cocktail was added and after 4 hours the bound radioactivity was determined by counting (4 min) in a Beckman liquid scintillation counter.
Data analysis Data are analysed using GraphPad prism and the general equation for a competition curve with variable Hill slope (n$_H$).

$Y$=Non-specific binding+(Total binding−Non-specific binding)/1+$10^{((logIC_{50}-X)\cdot nH)}$ where
X is the log concentration of competing compound,
Y is the binding obtained at each concentration of X,
$pIC_{50}$ is the concentration of the competitor required to compete for half of the specific binding.

The $IC_{50}$ is converted to the $K_1$ using the Cheng Prusoff equation, $$K_I = IC_{50}/(1+(L/K_D))$$

where $IC_{50}$ is the concentration of competitor required to compete for half the specific binding, L is the radioligand concentration used, $K_D$ is the equilibrium dissociation constant for the radioligand determined by saturation experiments.

The following results were obtained in the two assays:

| Example No. | $pK_B$ (functional assay) | $pK_1$ (binding assay) |
|---|---|---|
| 1 | 6.70 | 7.77 |
| 2 | 5.62 | |
| 3 | 6.27 | |
| 4 | 6.40 | |
| 6 | 6.96 | 7.50 |
| 7 | 6.81 | 7.42 |
| 8 | 7.11 | 7.49 |
| 9 | 7.33 | 7.94 |
| 10 | 8.62 | 8.53 |
| 11 | 8.01 | 7.95 |
| 12 | 8.20 | 8.23 |
| 13 | 8.68 | 8.56 |
| 14 | 7.04 | 7.28 |
| 15 | 8.77 | 8.36 |
| 16 | 6.77 | |
| 17 | 6.35 | |
| 18 | 6.79 | |
| 19 | <5.0 | 5.95 |
| 20 | <5.50 | 7.26 |
| 21 | <5.0 | 5.54 |
| 23 | 5.87 | 7.55 |
| 26 | 6.29 | |
| 27 | 5.11 | |
| 28 | 5.39 | |
| 29 | 6.88 | 7.40 |
| 30 | 6.62 | 6.97 |
| 31 | 5.79 | 7.07 |
| 32 | 7.36 | 7.44 |
| 33 | 6.64 | 7.27 |
| 34 | | 7.23 |
| 35 | 5.59 | |
| 36 | 6.16 | |
| 37 | 5.71 | |
| 38 | 8.37 | 8.15 |
| 39 | 7.37 | 7.80 |
| 40 | | 6.02 |
| 41 | 8.41 | 8.37 |
| 42 | 7.86 | 7.79 |
| 43 | 6.42 | 7.25 |
| 44 | 8.49 | 8.68 |
| 45 | 8.91 | 8.71 |
| 46 | 7.70 | 7.84 |
| 47 | 8.48 | 8.57 |
| 48 | 7.06 | 7.58 |
| 49 | 8.32 | 8.12 |
| 50 | 7.73 | 7.78 |
| 51 | 7.01 | 7.10 |
| 52 | | 6.70 |
| 53 | 6.74 | 7.25 |
| 54 | 7.80 | 8.00 |
| 55 | 8.22 | 8.11 |
| 56 | 6.35 | 6.86 |
| 57 | 7.96 | 7.84 |
| 58 | 8.98 | 8.36 |
| 59 | 8.43 | 8.08 |
| 60 | 7.84 | 8.34 |
| 61 | 8.62 | 8.46 |
| 62 | 8.13 | 8.24 |
| 63 | 8.39 | 8.18 |
| 64 | 8.41 | 8.30 |
| 65 | 7.32 | 7.98 |
| 66 | 8.06 | 8.11 |
| 67 | 6.22 | 6.85 |
| 68 | 7.77 | 7.95 |
| 69 | 8.92 | 8.73 |
| 70 | 7.80 | 7.95 |
| 71 | $p[A]_{50} = 6.11$ | 8.44 |
| 72 | 6.02 | |
| 73 | 4.99 α~20% | |
| 77 | | 8.51 |
| 78 | | 8.45 |
| 79 | | 8.13 |
| 80 | | 6.76 |
| 81 | | 6.84 |
| 82 | | 7.56 |
| 84 | 8.10 | |
| 85 | 8.05 | |

Typical variance in the functional assay is ±0.15 log units. Typical variance in the binding assay is ±0.12 log units. This means that if the discrepancy between the two assays is greater than about 0.5 log units, then this difference on average is significant.

What is claimed is:

1. A compound of the formula

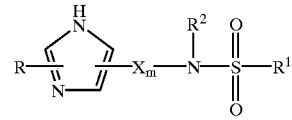

or

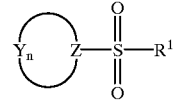

wherein

R represents from zero to two substituents, selected from the groups consisting of $C_1$ to $C_6$alkyl, $C_1$ to $C_6$ alkoxy, $C_1$ to $C_6$alkylthio, carboxy, $C_1$ to $C_6$carboalkoxy, nitro, trihalomethyl, hydroxy, amino, $C_1$ to $C_6$alkylamino, di($C_1$ to $C_6$alkyl)amino, aryl, $C_1$ to $C_6$ alkylaryl, halo, sulphamoyl and cyano, $R^1$ is $C_4$ to $C_{20}$ hydrocarbyl unsubstituted or substituted by halogen, and up to four carbon atoms are unsubstituted or substituted by oxygen, nitrogen or sulphur atoms, provided that $R^1$ does not contain an —O—O— group), $R^2$ is H or $C_1$ to $C_{15}$ hydrocarbyl unsubstituted or substituted by halogen, and up to three carbon atoms are unsubstituted or substituted by oxygen, nitrogen or sulphur atoms, provided that $R^2$ does not contain an —O—O— group), m is an integer from 3 to 9

41 n is an integer from 2 to 6, each X group is independently

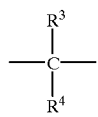

or one X group is —N(R$^4$)—, —O— or —S— (provided that this X group is not adjacent the —NR$^2$— group) and the remaining X groups are independently

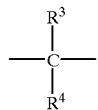

wherein R$^3$ is H, C$_1$ to C$_6$alkyl, C$_2$to C$_6$alkenyl, —CO$_2$R$^5$, —CONR$^5$$_2$, —CR$^5$$_2$OR$^6$ or —OR$^5$ (in which R$^5$ and R$^6$ are H or C$_1$ to C$_3$ alkyl), and R$^4$ is H or C$_1$ to C$_6$ alkyl, provided that R$^3$ is not —CO$_2$H and further provided that

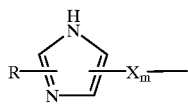

is not

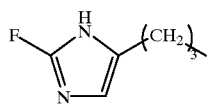

each Y group is independently —C(R$^3$)R$^4$—, or up to two Y groups are —N(R$^4$)—, —O— or —S— and the remaining Y groups are independently —C(R$^3$)R$^4$—, wherein R$^3$ is as defined above, one R$^4$ group in the structure is imidazoyl, imidazoylalkyl, substituted imidazoyl or substituted imidazoylalkyl, and the remaining R$^4$ groups are H or C$_1$ to C$_6$alkyl, and Z is >C(R$^7$)NR$^2$— or >N—, wherein R$^7$ is any of the groups recited above for R$^3$, or a pharmaceutically acceptable salt thereof.

2. A compound according to claim 1 having the formula

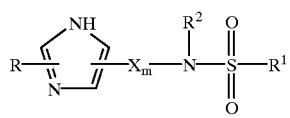

wherein —X$_m$— is attached to the 4- or 5-position of the imidazole ring.

3. A compound according to claim 2 wherein —X$_m$— is a C$_3$ to C$_9$ alkylene group.

4. A compound according to claim 1 wherein R$^2$ is H, C$_1$ to C$_6$ alkyl, C$_1$ to C$_6$ cycloalkyl, C$_1$ to C$_6$ hydroxyalkyl, C$_1$ to C$_6$ alkylhydroxyalkyl, aryl C$_1$ to C$_6$ alkyl or substituted aryl C$_1$ to C$_6$ alkyl.

5. A compound according to claim 4 wherein R$^2$ is hydrogen or C$_1$ to C$_3$ alkyl.

42

6. A compound according to claim 1 wherein R$^1$ is a group of the formula

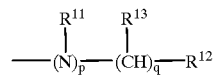

wherein p is 0 or 1,

R$^{11}$ is H or C$_1$ to C$_3$ alkyl, q is from 0 to 4,

R$^{12}$ is a carbocyclic, substituted carbocyclic, heterocyclic or substituted heterocyclic group, and R$^{13}$ is independently selected from H, C$_1$ to C$_6$ alkyl, C$_1$ to C$_6$ cycloalkyl, C$_1$ to C$_6$ hydroxyalkyl, C$_1$ to C$_6$ alkylhydroxyalkyl, aryl C$_1$ to C$_6$ alkyl and substituted aryl C$_1$ to C$_6$ alkyl.

7. A compound according to claim 6 wherein R$^{13}$ is H.

8. A compound according to claim 1 wherein R$^1$ contains an aryl or substituted aryl group.

9. A compound according to claim 8 wherein the aryl group is phenyl or substituted phenyl.

10. A compound according to claim 8 wherein the aryl group is naphthyl or substituted naphthyl.

11. A compound according to claim 1 having the formula

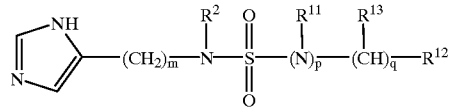

wherein m is from 3 to 10,

R$^2$ and R$^{11}$ are independently H or methyl, p is 0 or 1, q is from 0 to 3, R$^{12}$ is selected from 2-naphthyl, phenyl, 4-chlorophenyl, 3,4-dichlorophenyl, 2-chlorophenyl, 3-chlorophenyl, 4-iodophenyl, 4-bromophenyl, 4-fluorophenyl, 4-(trifluoromethyl)phenyl, 4-methoxyphenyl, 4-biphenyl, cyclohexyl and adamantyl, and R$^{13}$ is independently selected from H, methyl and phenyl.

12. A compound according to claim 1 wherein R$^1$ is a (cycloalkyl)alkyl group.

13. A compound according to claim 12 wherein the (cycloalkyl)alkyl group is cyclohexylpropyl or adamantylpropyl.

14. A compound which is degraded in vivo to yield a compound according to claim 1.

15. A pharmaceutical composition comprising a compound according to claim 1 and a pharmaceutically acceptable excipient or carrier.

16. A method of making a compound according to claim 1, said method comprising reacting a suitably protected derivative of a compound of the formula

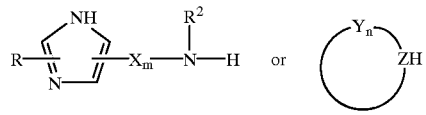

with a sulfonyl chloride of the formula R$^1$SO$_2$Cl, wherein R, R$^1$, R$^2$, X, Y, Z, m and n are as defined in claim 1.

17. A method of making a sulfamide compound according to claim 1, said method comprising the steps of
a) reacting chlorosulfonyl isocyanate with an appropriate alcohol,
b) reacting the product of step a) with a suitably protected derivative of a compound of the formula

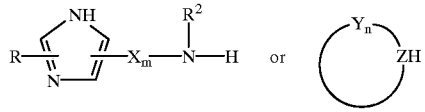   or   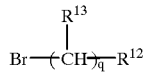

c) reacting the product of step b) with a base such as sodium hydride and then a compound of formula $R^1$—Br, wherein the bromine atom is attached to a carbon atom of $R^1$, and
d) treating the product of step c) with acid,
wherein R, $R^1$, X, Y, Z, m, n and $R^2$ are as defined in claim 1.

18. A method according to claim 17 wherein the compound of formula $R^1$—Br used in step c) is of the formula $$Br\text{—}(CH)_q\text{—}R^{12}$$
with $R^{13}$ on the CH wherein
q is from 0 to 4,
$R^{12}$ is a carbocyclic, substituted carbocyclic, heterocyclic or substituted heterocyclic group, and
$R^{13}$ is independently selected from H, $C_1$ to $C_6$ alkyl, $C_1$ to $C_6$ cycloalkyl, $C_1$ to $C_6$ hydroxyalkyl, $C_1$ to $C_6$ alkylhydroxyalkyl, aryl $C_1$ to $C_6$ alkyl and substituted aryl $C_1$ to $C_6$ alkyl.

19. A method of making a sulfamide compound according to claim 1, said method comprising the steps of
a) reacting chlorosulfonyl isocyanate with an appropriate alcohol,
b) reacting the product of step a) with a suitably protected derivative of a compound of the formula $R^1$—H, wherein the hydrogen atom is attached to a nitrogen atom of $R^1$,
c) reacting the product of step b) with a suitably protected derivative of a compound of formula

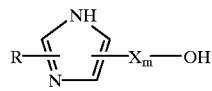

and
d) treating the product of step c) with acid,
wherein R, $R^1$, X and m are as defined in claim 1.

20. A method according to claim 19 wherein the compound of formula $R^1$—H used in step b) is of the formula

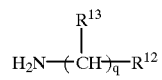

wherein
q is from 0 to 4,
$R^{12}$ is a carbocyclic, substituted carbocyclic, heterocyclic or substituted heterocyclic group, and
$R^{13}$ is independently selected from H, $C_1$ to $C_6$ alkyl, $C_1$ to $C_6$ cycloalkyl, $C_1$ to $C_6$ hydroxyalkyl, $C_1$ to $C_6$alkylhydroxyalkyl, aryl $C_1$ to $C_6$ alkyl and substituted aryl $C_1$ to $C_6$ alkyl.

21. A method of producing an antihistamine effect in a patient in need thereof, comprising administering an effective amount of the compound of claim 1.

22. A method of treatment of a disease associated with the $H_3$ receptor site, comprising administering to a patient in need thereof an amount of a compound of claim 1 effective to block the $H_3$ receptor site.

23. A method according to claim 22, wherein the disease is selected from the group consisting of sleep irregularity, convulsions, conditions resulting from irregular hypothalamo-hypophyseal secretion, depression, abnormal cerebral circulation, asthma and irritable bowel syndrome.

* * * * *